(12) United States Patent
Uchiyama et al.

(10) Patent No.: US 9,744,294 B2
(45) Date of Patent: Aug. 29, 2017

(54) PUNCTURE DEVICE AND CHEMICAL LIQUID SUPPLYING DEVICE

(71) Applicant: Terumo Kabushiki Kaisha, Tokyo (JP)

(72) Inventors: Joji Uchiyama, Kanagawa (JP); Hiromasa Kohno, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 392 days.

(21) Appl. No.: 14/491,300

(22) Filed: Sep. 19, 2014

(65) Prior Publication Data
US 2015/0005710 A1 Jan. 1, 2015

Related U.S. Application Data

(63) Continuation of application No. PCT/JP2013/001870, filed on Mar. 19, 2013.

(30) Foreign Application Priority Data

Mar. 22, 2012 (JP) ................ 2012-065271

(51) Int. Cl.
*A61M 1/00* (2006.01)
*A61M 5/158* (2006.01)
(Continued)

(52) U.S. Cl.
CPC ........ *A61M 5/158* (2013.01); *A61M 5/14248* (2013.01); *A61M 5/1582* (2013.01);
(Continued)

(58) Field of Classification Search
CPC ............ A61M 5/14248; A61M 5/1582; A61M 5/1452; A61M 2005/1583;
(Continued)

(56) References Cited

U.S. PATENT DOCUMENTS 6,413,238 B1 * 7/2002 Maget ............... A61M 5/14526
604/132
2001/0027292 A1 * 10/2001 Tamura ................. A61M 5/158
604/110
(Continued)

FOREIGN PATENT DOCUMENTS

| JP | 62-009448 U | 1/1987 |
|---|---|---|
| JP | 2002-058747 A | 2/2002 |
| JP | 2007-510499 A | 4/2007 |
| JP | 2010-501283 A | 1/2010 |
| JP | 2010-046204 A | 3/2010 |
| JP | 2011-147551 A | 8/2011 |
| WO | WO-2005/046781 A1 | 5/2005 |

*Primary Examiner* — Kevin C Sirmons
*Assistant Examiner* — Leah Swanson
(74) *Attorney, Agent, or Firm* — Foley & Lardner LLP

(57) ABSTRACT

A puncture device includes a puncture needle including an outer needle and an inner tube located in the outer needle; a housing unit accommodating the puncture needle; and a puncture mechanism within the housing unit. The puncture mechanism includes a push-in unit configured to be pushed in with respect to the housing unit, an outer needle slide unit attached to the outer needle, a stopper, an elastic member, a first end of which is fixed to the housing unit and a second end of which is fixed to the outer needle slide unit, and a fixation release unit configured to release the fixation between the push-in unit and the outer needle slide unit and the fixation between the outer needle slide unit and the inner tube.

20 Claims, 23 Drawing Sheets

(51) Int. Cl.
*A61M 5/142* (2006.01)
*A61M 5/145* (2006.01)

(52) U.S. Cl.
CPC ... *A61M 5/1452* (2013.01); *A61M 2005/1583* (2013.01); *A61M 2005/1585* (2013.01); *A61M 2205/02* (2013.01); *A61M 2205/502* (2013.01); *A61M 2205/52* (2013.01)

(58) Field of Classification Search
CPC ........... A61M 2005/1585; A61M 2005/14252; A61M 2005/1587
USPC ........................................................ 604/151
See application file for complete search history.

(56) References Cited

U.S. PATENT DOCUMENTS

| | | | |
|---|---|---|---|
| 2007/0088277 A1* | 4/2007 | McGinley | A61B 17/3462 604/167.01 |
| 2007/0282269 A1* | 12/2007 | Carter | A61M 5/14248 604/164.01 |
| 2009/0036870 A1 | 2/2009 | Mounce et al. | |
| 2010/0049129 A1 | 2/2010 | Yokoi et al. | |
| 2010/0217105 A1 | 8/2010 | Yodfat et al. | |
| 2010/0324392 A1* | 12/2010 | Yee | A61B 5/14532 600/345 |

\* cited by examiner

FIG. 5
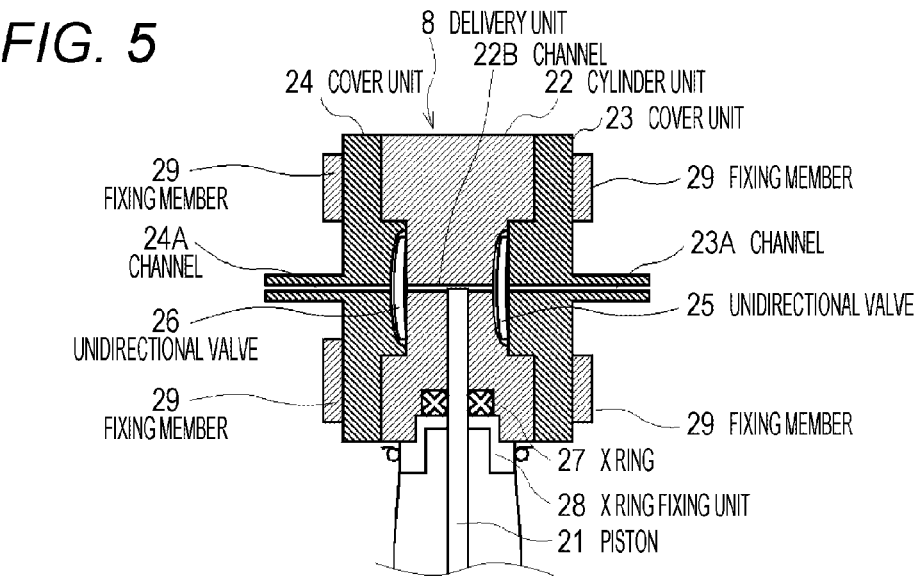
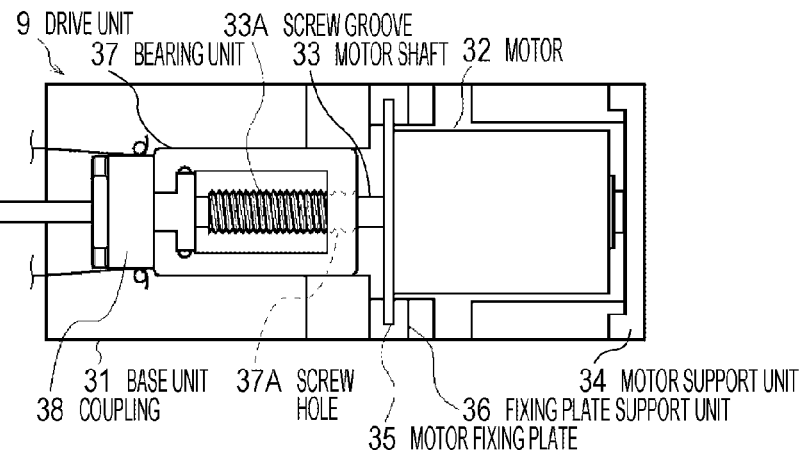
FIG 6A
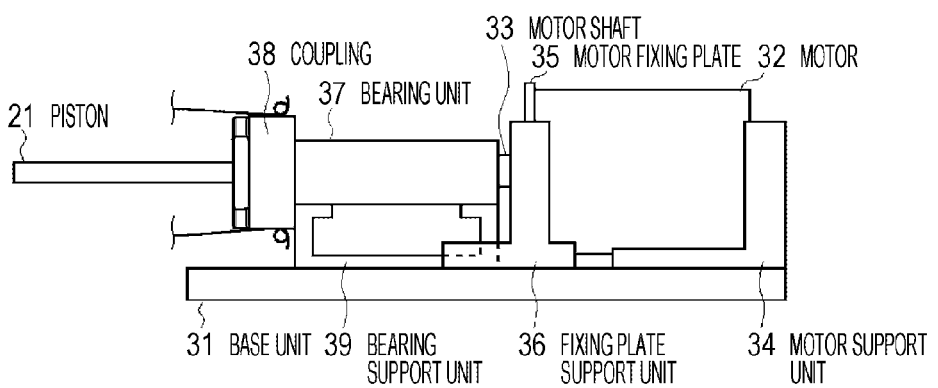
FIG 6B

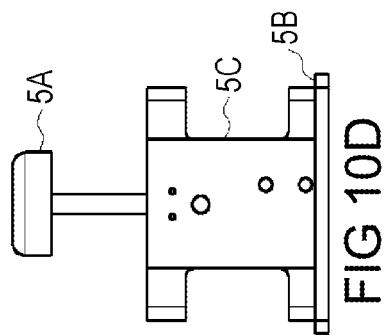
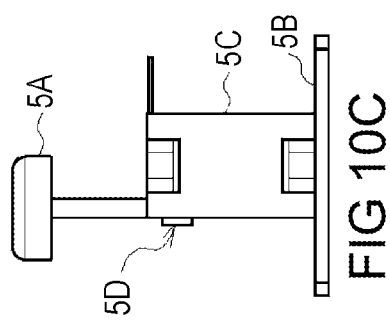
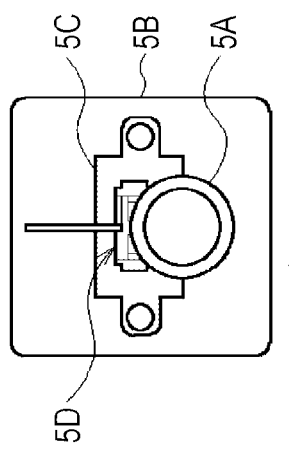
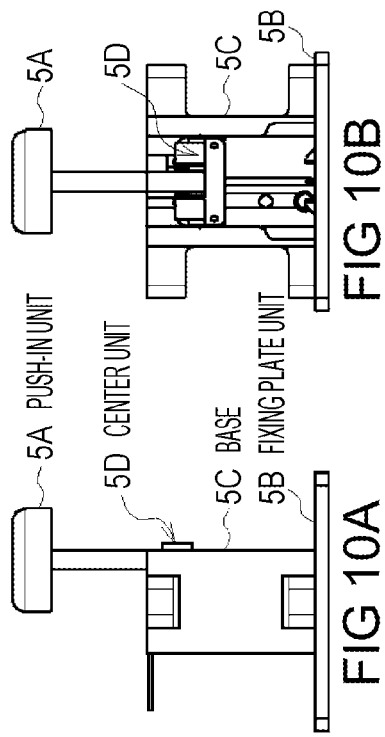
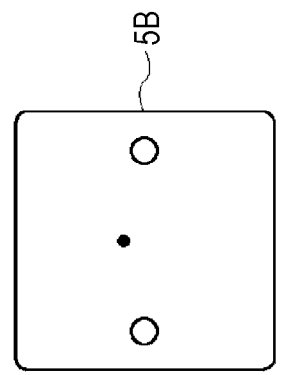

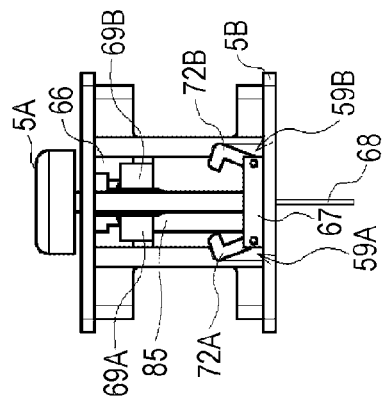
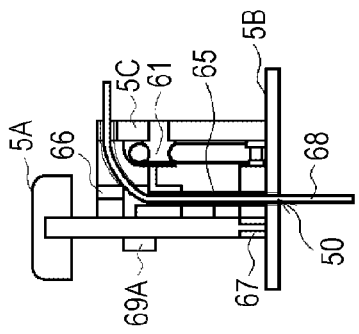
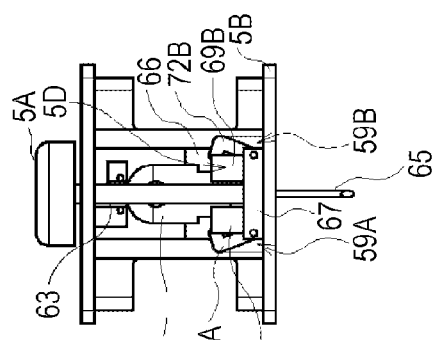
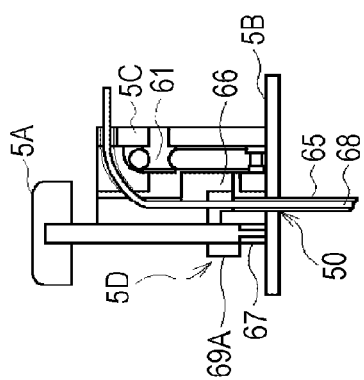
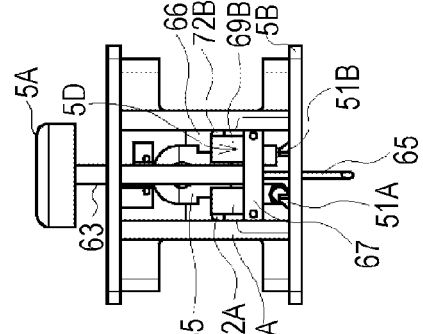
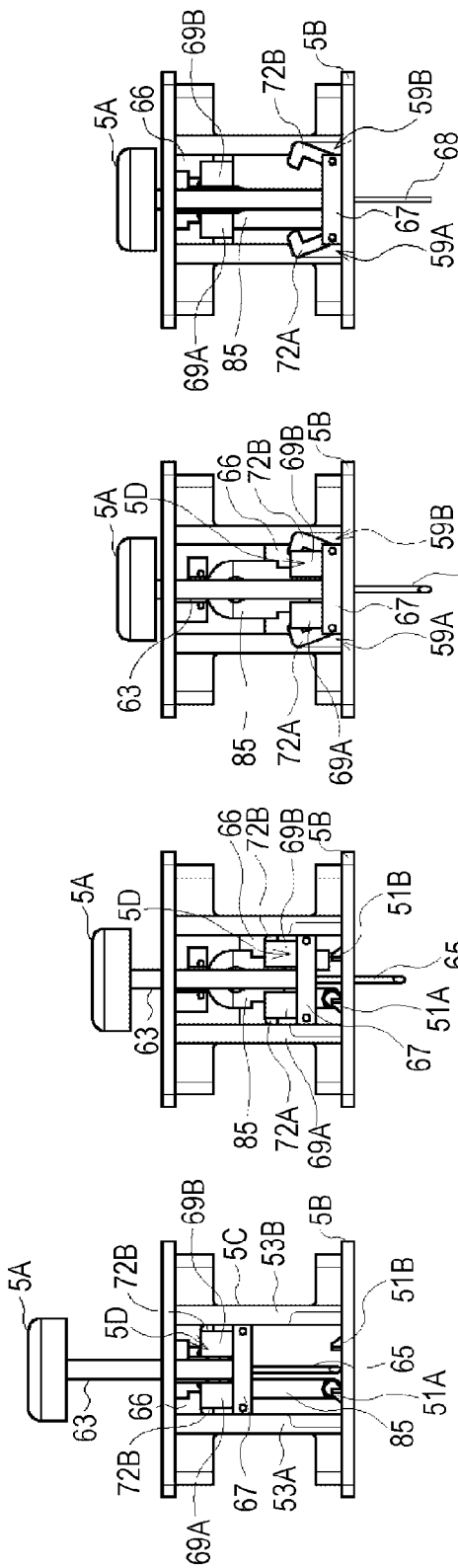
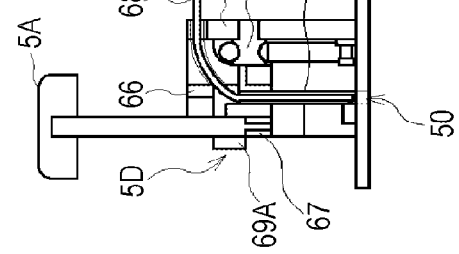

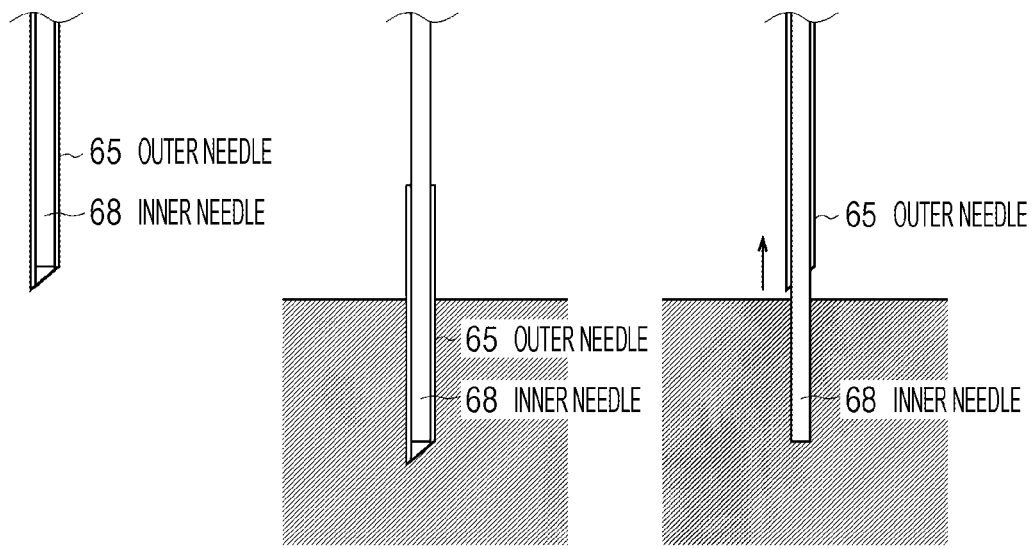
FIG 17A  FIG 17B  FIG 17C
*FIG. 18*
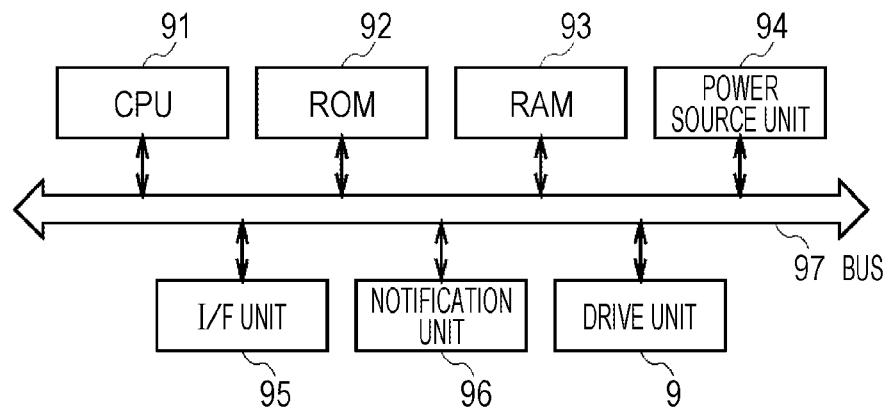

100 SENSOR DEVICE
101 CONTROLLER
102 TRANSMISSION UNIT
5 PUNCTURE MECHANISM

65 OUTER NEEDLE
68 INNER NEEDLE
104 SIGNAL LINE
103 SENSOR

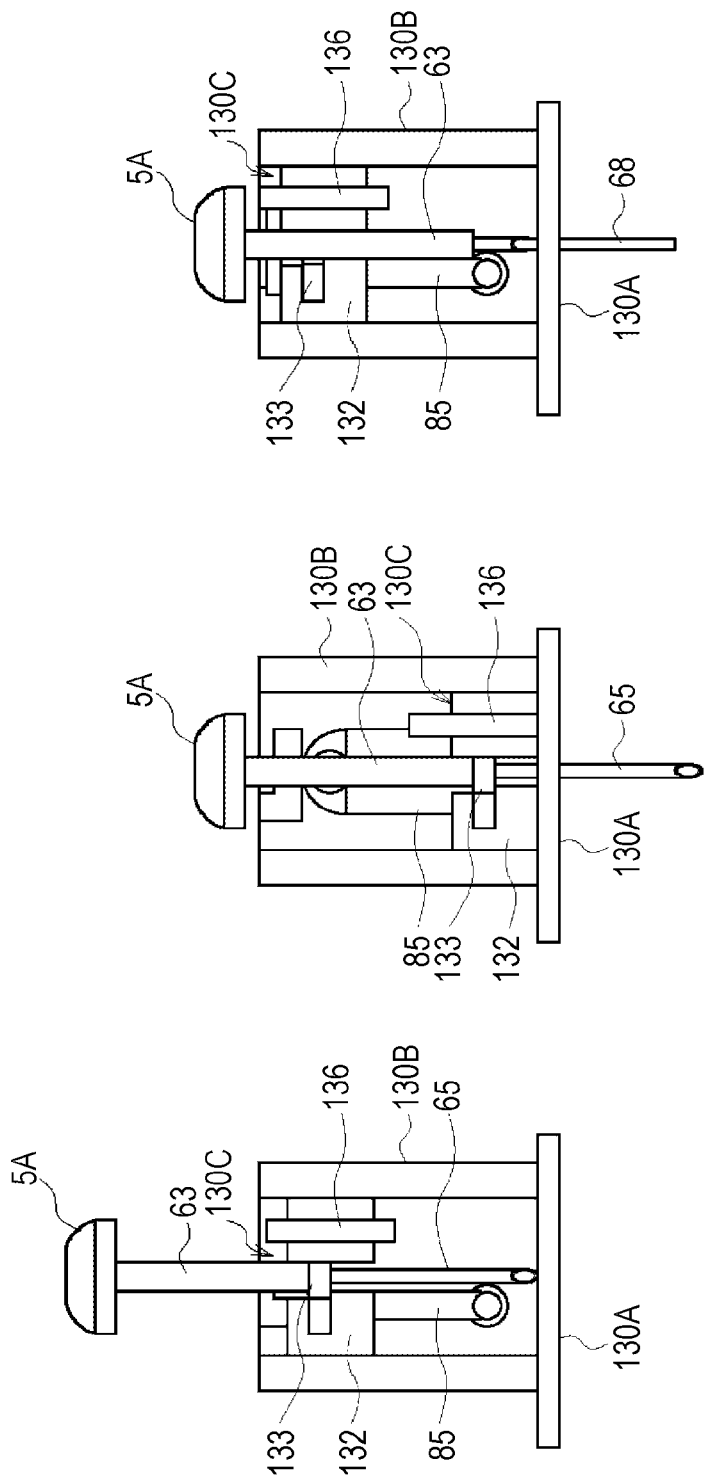

PUNCTURE DEVICE AND CHEMICAL LIQUID SUPPLYING DEVICE

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/001870 filed on Mar. 19, 2013, which is based upon and claims the benefit of priority of Japanese Application No. 2012-065271 filed on Mar. 22, 2012, the entire contents of which are hereby incorporated by reference in their entireties.

BACKGROUND

Technical Field

The present disclosure relates to a puncture device and a chemical liquid supplying device, and particularly suited for supply of insulin into a body, for example.

Background Art

A so-called syringe pump type chemical liquid supplying device has been proposed as a device for supplying chemical liquid (insulin). This type of chemical liquid supplying device is a portable device attached to the skin of a user during use, and supplies chemical liquid into the body of the user by using a plunger which pushes the chemical liquid out of an outer cylinder filled with the chemical liquid (for example, see JP 2010-501283 A).

The chemical liquid supplying device supplies chemical liquid via a puncture needle inserted into the body of the user. As a structure of this type of puncture needle, there has been proposed a puncture needle having a double structure of a metal inner needle and a plastic outer needle (for example, see JP 2002-58747 A).

According to this type of puncture needle having a double structure, the metal inner needle projected from the tip of the plastic outer needle is inserted into the body of the user. Then, the metal inner needle is removed from the plastic outer needle. In this condition, chemical liquid is supplied via the outer needle as the only needle indwelled inside the body of the user.

According to the conventional puncture needle having a double structure, the outer needle functions as an indwelled needle to be indwelled within the body of the user.

When the diameter of the indwelled needle becomes smaller, the pain given to the user may decrease. However, according to the conventional puncture needle which inserts the metal inner needle into the outer needle functioning as the indwelled needle, the inside diameter of the outer needle functioning as the indwelled needle needs to be larger than the outside diameter of the metal inner needle. In this case, reduction of the diameter of the indwelled needle is difficult.

SUMMARY OF THE INVENTION

It is expected herein that the burden imposed on the user may be considerably reduced when the diameter of the indwelled needle of the puncture needle having the double structure decreases.

Embodiments of the present invention have been developed in consideration of the aforementioned points. Proposed herein are a puncture device and a chemical liquid supplying device capable of considerably reducing the burden imposed on the user.

A puncture device according to one embodiment of the present invention includes: a puncture needle having a double structure including a metal outer needle and a resin inner needle inserted into the outer needle; a housing unit accommodating the puncture needle; and a puncture mechanism provided within the housing unit, the puncture mechanism allowing the puncture needle to project from the housing unit with the inner needle inserted into the outer needle, inserting the projected puncture needle into the body of a user, and then retracting only the outer needle of the puncture needle into the housing unit with the inner needle of the puncture needle indwelled within the body. The puncture mechanism includes a push-in unit capable of being pushed in with respect to the housing unit, an outer needle slide unit provided with the outer needle and capable of sliding within the housing unit, a stopper making fixation between the push-in unit and the outer needle slide unit, and fixation between the inner needle inserted into the outer needle and the outer needle slide unit, an elastic member one end of which is fixed to the housing unit and the other end of which is fixed to the outer needle slide unit, and a fixation release unit releasing the fixation between the push-in unit and the outer needle slide unit, and the fixation between the outer needle slide unit and the inner needle, both of which fixations are made by the stopper. When the push-in unit is pushed in under the condition of fixation between the push-in unit and the outer needle slide unit, and fixation between the outer needle slide unit and the inner needle, both of which fixations are made by the stopper, the outer needle containing the inner needle inside projects from the housing unit and is inserted into the body of the user in accordance with sliding of the outer needle slide unit. When the outer needle slide unit slides to a predetermined position, only the outer needle is retracted into the housing unit with the inner needle indwelled within the body in accordance with release of the fixation between the push-in unit and the outer needle slide unit and the fixation between the outer needle slide unit and the inner needle, and sliding of the outer needle slide unit in another direction by operation of the elastic member.

Moreover, a chemical liquid supplying device according to one embodiment of the present invention includes: a puncture needle having a double structure including a metal outer needle and a resin inner needle inserted into the outer needle; a housing unit accommodating the puncture needle; a puncture mechanism provided within the housing unit, the puncture mechanism allowing the puncture needle to project from the housing unit with the inner needle inserted into the outer needle, inserting the projected puncture needle into the body of a user, and then retracting only the outer needle of the puncture needle into the housing unit with the inner needle of the puncture needle indwelled within the body; a chemical liquid storage unit storing chemical liquid; and a delivery unit delivering chemical liquid stored in the chemical liquid storage unit into the body via the inner needle indwelled within the body. The puncture mechanism includes a push-in unit capable of being pushed in with respect to the housing unit, an outer needle slide unit provided with the outer needle and capable of sliding within the housing unit, a stopper making fixation between the push-in unit and the outer needle slide unit and fixation between the inner needle inserted into the outer needle and the outer needle slide unit, an elastic member one end of which is fixed to the housing unit and the other end of which is fixed to the outer needle slide unit, and a fixation release unit releasing the fixation between the push-in unit and the outer needle slide unit and the fixation between the outer needle slide unit and the inner needle, both of which fixations are made by the stopper. When the push-in unit is pushed in under the condition of fixation between the push-in unit and the outer needle slide unit and fixation between the outer needle slide unit and the inner needle, both of which fixations are made by the stopper, the outer needle containing the inner needle inside projects from the housing unit and is inserted into the body of the user in accordance with sliding of the outer needle slide unit. When the outer needle slide unit slides to a predetermined position, only the outer needle is retracted into the housing unit with the inner needle indwelled within the body in accordance with release of the fixation between the push-in unit and the outer needle slide unit and the fixation between the outer needle slide unit and the inner needle and sliding of the outer needle slide unit in another direction by operation of the elastic member.

As described herein, the indwelled needle is the inner needle of the puncture needle having the double structure of the outer needle and the inner needle. Accordingly, the diameter of the indwelled needle can be easily made smaller in comparison with a conventional puncture needle whose indwelled needle is the outer needle. Moreover, processes from insertion of the puncture needle to retraction of the outer needle can be performed at a time only by push-in operation of the push-in unit.

According to certain embodiments of the present invention, a needle functioning as an indwelled needle is an inner needle of a puncture needle having a double structure of an outer needle and the inner needle. Accordingly, the diameter of the indwelled needle can be easily made smaller in comparison with a conventional puncture needle whose indwelled needle is the outer needle. Moreover, processes from insertion of the puncture needle to retraction of the outer needle can be performed at a time only by push-in operation of a push-in unit. Accordingly, a puncture device and a chemical liquid supplying device provided according to certain embodiments of the present invention can considerably reduce a burden imposed on a user.

BRIEF DESCRIPTION OF THE DRAWINGS

FIG. 5 is a diagram schematically illustrating a condition of a piston shifted to a push-end position.

FIG. 6A is a top perspective view schematically illustrating the structure of a drive unit.

FIG. 6B is a side perspective view schematically illustrating the structure of a drive unit.

FIG. 10A is a left side view diagram schematically illustrating the structure of the puncture mechanism.

FIG. 10B is a front view diagram schematically illustrating the structure of the puncture mechanism.

FIG. 10C is a right side view diagram schematically illustrating the structure of the puncture mechanism.

FIG. 10D is a rear view diagram schematically illustrating the structure of the puncture mechanism.

FIG. 10E is a top view diagram schematically illustrating the structure of the puncture mechanism.

FIG. 10F is a bottom side view diagram schematically illustrating the structure of the puncture mechanism.

FIG. 15A is a front perspective view of the puncture mechanism showing the push-in unit not pushed in.

FIG. 15B is a front perspective view of the puncture mechanism showing the push-in unit partially pushed in.

FIG. 15C is a front perspective view of the puncture mechanism showing the push-in unit pushed in and the outer needle slide unit being released.

FIG. 15D is a front perspective view of the puncture mechanism showing the push-in unit pushed in and the outer needle slide unit after it was released.

FIG. 15E is a side perspective view of the puncture mechanism showing the push-in unit not pushed in.

FIG. 15F is a side perspective view of the puncture mechanism showing the push-in unit partially pushed in.

FIG. 15G is a side perspective view of the puncture mechanism showing the push-in unit pushed in and the outer needle slide unit being released.

FIG. 15H is a side perspective view of the puncture mechanism showing the push-in unit pushed in and the outer needle slide unit after it was released.

FIG. 17A is a diagram schematically illustrating the structure of a puncture needle (outer needle and inner needle) showing the inner needle within the outer needle.

FIG. 17B is a diagram schematically illustrating the structure of a puncture needle (outer needle and inner needle) showing the inner needle within the outer needle after the puncture needle has been inserted.

FIG. 17C is a diagram schematically illustrating the structure of a puncture needle (outer needle and inner needle) showing the inner remaining inserted after the outer needle retracts.

FIG. 18 is a diagram schematically illustrating the electric structure of the chemical liquid supplying device.

FIG. 27A is a diagram schematically describing operation of the puncture mechanism according to the still further different embodiment in a first position.

FIG. 27B is a diagram schematically describing operation of the puncture mechanism according to the still further different embodiment in a second position.

FIG. 27C is a diagram schematically describing operation of the puncture mechanism according to the still further different embodiment in a third position.

DETAILED DESCRIPTION

An embodiment according to the present invention is hereinafter described in detail with reference to the drawings.

General Structure of Chemical Liquid Supplying Device

Figure 1A:
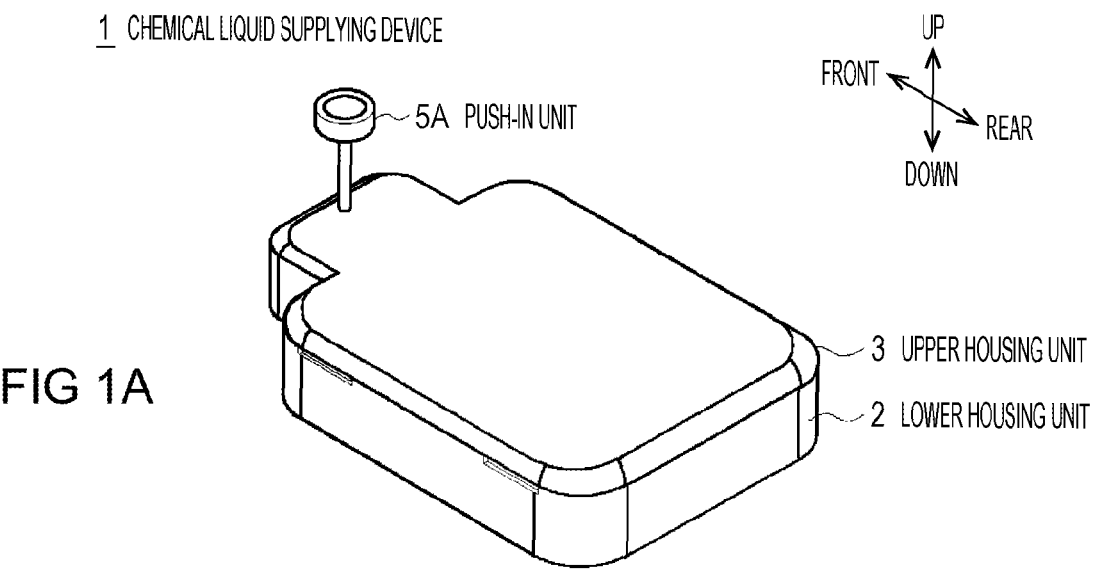
FIG. 1A is a top perspective view schematically illustrating the structure of a chemical liquid supplying device.
Figure 1B:
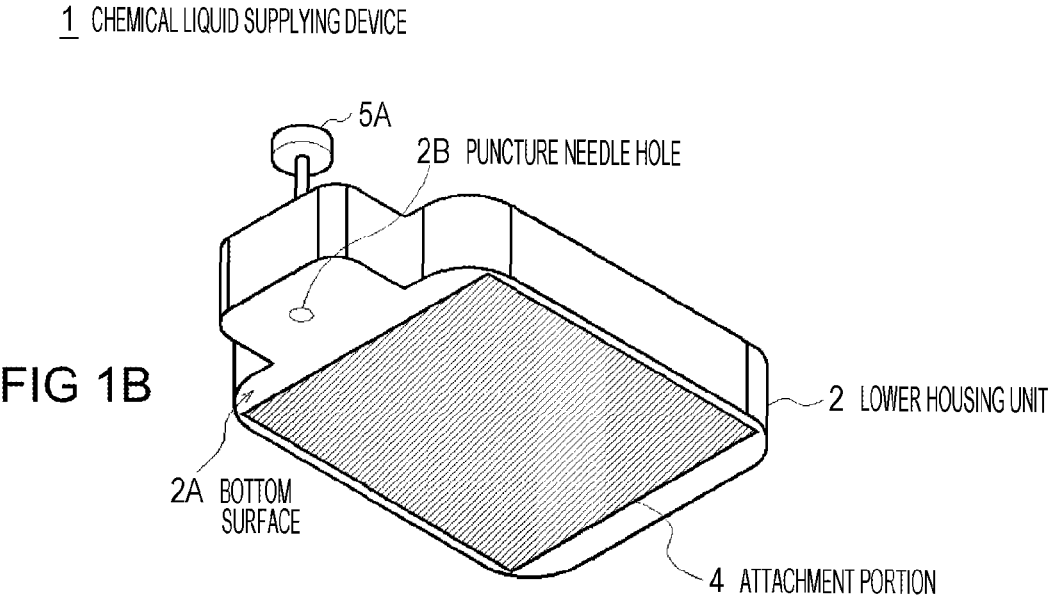
FIG. 1B is a bottom perspective view schematically illustrating the structure of a chemical liquid supplying device.
Figure 2:
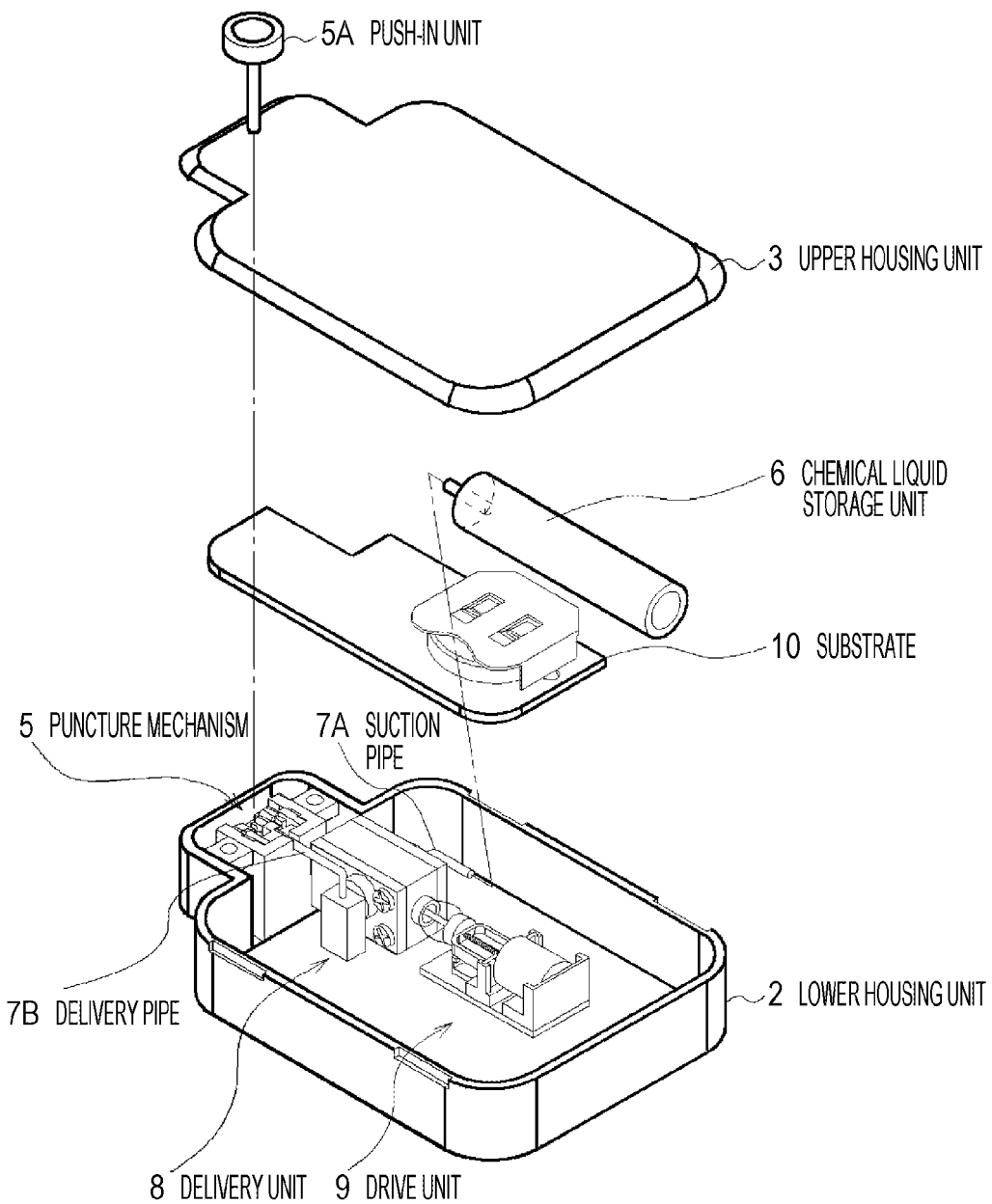
FIG. 2 is a perspective view schematically illustrating the disassembled chemical liquid supplying device.

As illustrated in FIGS. 1A-1B and FIG. 2, a chemical liquid supplying device 1 is a portable device attached to the skin of a user and held by the user during use. The chemical liquid supplying device 1 has a flat and substantially rectangular parallelepiped shape constituted by a lower housing unit 2 and an upper housing unit 3. The upper side of the lower housing unit 2 is opened. A space is formed inside the lower housing unit 2. The upper housing unit 3 is fitted to the opening of the lower housing unit 2.

The size of the chemical liquid supplying device 1 is only required to be small enough to allow attachment of the chemical liquid supplying device 1 to the skin of the user. For example, the chemical liquid supplying device 1 may have a substantially rectangular parallelepiped shape having a width of 32 mm, a depth of 44 mm, and a height of 11 mm.

An attachment portion 4 constituted by a double-sided tape or the like is provided on a bottom surface 2A of the lower housing unit 2. The chemical liquid supplying device 1 is held on the user by attachment of the attachment portion 4 to the skin of the user.

The chemical liquid supplying device 1 has a puncture needle hole 2B at the front end of the bottom surface 2A of the lower housing unit 2. The puncture needle hole 2B is a hole through which a puncture needle (not shown) is projected from a space formed between the lower housing unit 2 and the upper housing unit 3 by operation of a puncture mechanism 5. The puncture needle is a needle inserted into the body of the user to supply insulin, which has been charged into the chemical liquid supplying device 1, into the body of the user via the puncture needle. The puncture needle has a double structure constituted by a metal outer needle and a resin inner needle (or "inner tube"), as will be detailed later.

Moreover, the chemical liquid supplying device 1 has a push-in unit 5A at the front end of the upper housing unit 3. The push-in unit 5A is a unit capable of performing push-in operation. The push-in unit 5A is a part of the puncture mechanism 5 illustrated in FIG. 2. When the push-in unit 5A is pushed in by the user, the puncture mechanism 5 of the chemical liquid supplying device 1 actuated by this pushing allows the puncture needle to project from the puncture needle hole 2B, and inserts the puncture needle into the body of the user.

Furthermore, the chemical liquid supplying device 1 has a chemical liquid storage unit 6, a channel unit 7, a delivery unit 8, a drive unit 9, a substrate 10, and others. These components 6 to 9 are disposed in the space formed between the lower housing unit 2 and the upper housing unit 3.

The chemical liquid storage unit 6 is a unit provided with a cylindrical syringe outer cylinder 11 into which chemical liquid is charged from the outside, as will be detailed later.

The channel unit 7 includes a suction pipe 7A, a delivery pipe 7B, channels 22B, 23A, and 24A formed in the delivery unit 8, and an inner needle of the puncture needle contained in the puncture mechanism 5, and forms a channel through which chemical liquid flows from the chemical liquid storage unit 6 to the inside of the body. The suction pipe 7A connects the chemical liquid storage unit 6 and the channel 23A formed in the delivery unit 8 such that the chemical liquid storage unit 6 and the channel 23A can communicate with each other. The delivery pipe 7B connects the channel 24A formed in the delivery unit 8 and the inner needle of the puncture needle contained in the puncture mechanism 5 such that the channel 24A and the inner needle can communicate with each other.

The delivery unit 8 delivers chemical liquid stored in the chemical liquid storage unit 6 via the channel unit 7 into the body in accordance with sliding movement of a piston 21 within an inner space 22A of a cylinder unit 22 (FIGS. 4A-4B), as will be detailed later.

The drive unit 9 drives the piston 21 under the control of a CPU 91 (FIG. 18) such that the piston 21 can slide within the inner space 22A of the cylinder unit 22 in accordance with the control.

The substrate 10 is a unit on which a power source unit 94 for supplying source power (FIG. 18), the CPU 91, and other circuits are disposed.

Structure of Chemical Liquid Storage Unit

Figure 3A:
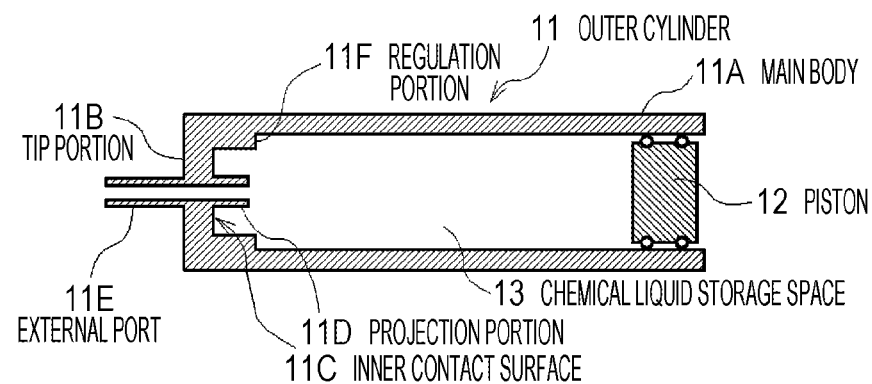
FIG. 3A is a diagram schematically illustrating the structure of a chemical liquid storage unit with the piston positioned away from the tip portion.
Figure 3B:
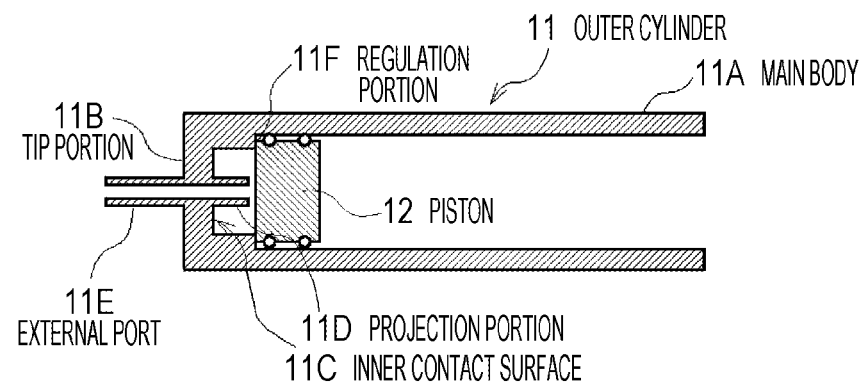
FIG. 3B is a diagram schematically illustrating the structure of a chemical liquid storage unit with the piton positioned near the tip portion.

As illustrated in FIGS. 3A-3B, in the chemical liquid storage unit 6, a piston 12 is inserted into the outer cylinder 11 having a cylindrical shape from an opened end of the outer cylinder 11. The chemical liquid storage unit 6 stores chemical liquid in a chemical liquid storage space 13 defined by the outer cylinder 11 and the piston 12.

The outer cylinder 11 has a tip portion 11B at the tip of a cylindrical main body 11A to close the tip of the main body 11A. The main body 11A and the tip portion 11B are formed integrally with each other.

The tip portion 11B has a hollow projection portion 11D which has an opening penetrating to the outside. The projection portion 11D is disposed at the center of a surface (hereinafter referred to as inner contact surface as well) 11C which contacts the chemical liquid storage space 13 in the direction perpendicular to the direction along the axis of the main body 11A (hereinafter referred to as cylinder axis direction as well).

The tip portion 11B has an external port 11E which communicates with the projection portion 11D and projects in the direction opposite to the projection direction of the projection portion 11D. The suction pipe 7A connects with the external port 11E.

The main body 11A has a regulation portion 11F projecting toward the inside from the inner circumferential surface constituting the main body 11A and contacting the chemical liquid storage space 13. The regulation portion 11F is a part which projects longer from the inner contact surface 11C than the projection portion 11D. In other words, the regulation portion 11F of the main body 11A is configured to have an inside diameter shorter than the inside diameter of the area of the main body 11A other than the regulation portion 11F.

The piston 12 is inserted into the outer cylinder 11 from the distal end of the piston 12 on the side opposite to the tip portion 11B. The piston 12 is disposed in such a position as to contact the inside surface of the main body 11A in the circumferential direction, and liquid-tightly slide in the cylinder axis direction of the main body 11A. The diameter of the piston 12 is larger than the inside diameter of the regulation portion 11F.

Chemical liquid stored in a vial is injected into the chemical liquid storage space 13 of the chemical liquid storage unit 6 through a predetermined injection port (not shown) with the piston 12 positioned closest to the tip portion 11B and contacting the regulation portion 11F. In this state, a small space is formed between the inner contact surface 11C of the outer cylinder 11 and the piston 12 in the chemical liquid storage unit 6 by the presence of the regulation portion 11F.

The chemical liquid storage unit 6 receives injection of a predetermined amount (such as 2 ml) of chemical liquid by the shift of the piston 12 toward the distal end in accordance with the injection of the chemical liquid. In this state, bubbles existing beforehand in the chemical liquid storage space 13 remain as they are in the chemical liquid storage space 13.

In delivery of chemical liquid into the body by operation of the delivery unit 8, the chemical liquid storage unit 6 delivers chemical liquid from the projection portion 11D and the external port 11E to the suction pipe 7A while shifting the piston 12 toward the tip portion 11B in accordance with chemical liquid suction pressure produced by the delivery unit 8. The chemical liquid storage unit 6 delivers chemical liquid until the piston 12 contacts the projection portion 11D.

When bubbles exist within the chemical liquid storage space 13 of the chemical liquid storage unit 6, most of the bubbles adhere to the wall surface of the chemical liquid storage unit 6. In this case, the bubbles adhering to the side surface of the main body 11A of the chemical liquid storage unit 6 are moved by the press of the piston 12 during delivery of chemical liquid in accordance with the shift of the piston 12. These bubbles stay in the space formed between the piston 12 and the inner contact surface 11C when the piston 12 contacts the regulation portion 11F. This avoids delivery of the bubbles to the outside.

Moreover, the projection portion 11D of the chemical liquid storage unit 6 projects toward the chemical liquid storage space 13 side from the inner contact surface 11C. This avoids delivery of the bubbles through the opening of the projection portion 11D to the outside from the side surface of the main body 11A to which the bubbles are adhering at the time of delivery of chemical liquid.

Structure of Delivery Unit

Figure 4A:
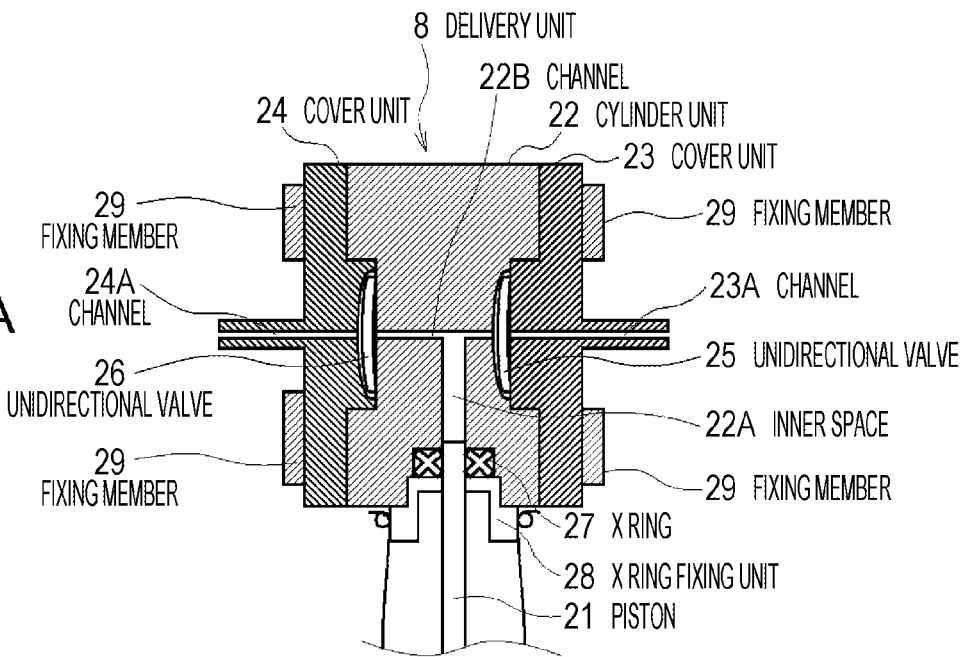
FIG. 4A is a diagram schematically illustrating the structure of a delivery unit.

As illustrated in FIG. 4A, the delivery unit 8 is configured to include the piston 21, the cylinder unit 22, cover units 23 and 24, unidirectional valves 25 and 26, an X ring 27, an X ring fixing unit 28, and fixing members 29.

The piston 21 has a diameter of 1.03 mm, for example, and slides by the drive of the drive unit 9 with predetermined strokes within the inner space 22A formed in the cylinder unit 22 and having a hollow cylindrical shape. Examples of the material of the piston 21 include stainless steel, copper alloy, aluminum alloy, titanium material, and thermoplastics elastomer such as polypropylene and polycarbonate.

The cylinder unit 22 has the inner space 22A into which the piston 21 is inserted from one end of the inner space 22A and slides within the inner space 22A. Moreover, the cylinder unit 22 has the channel 22B contacting the other end of the inner space 22A and configured to extend in the direction perpendicular to the inner space 22A and penetrate the opposed side surfaces of the cylinder unit 22.

The cylinder unit 22 has the X ring 27 and the X ring fixing unit 28 at the one end of the inner space 22A from which the piston 21 is inserted. The X ring 27 prevents leakage of chemical liquid between the one end of the inner space 22A and the piston 21. The X ring fixing unit 28 fixes the X ring 27.

The X ring 27 is inserted into the cylinder unit 22 from the surface side of the cylinder unit 22 where the inner space 22A is formed, and fixed by the press of the X ring fixing unit 28. The X ring fixing unit 28 fixes the X ring 27 with a part of the X ring fixing unit 28 fitted into the cylinder unit 22, and with the rest of the X ring fixing unit 28 exposed to the outside.

Figure 4B:
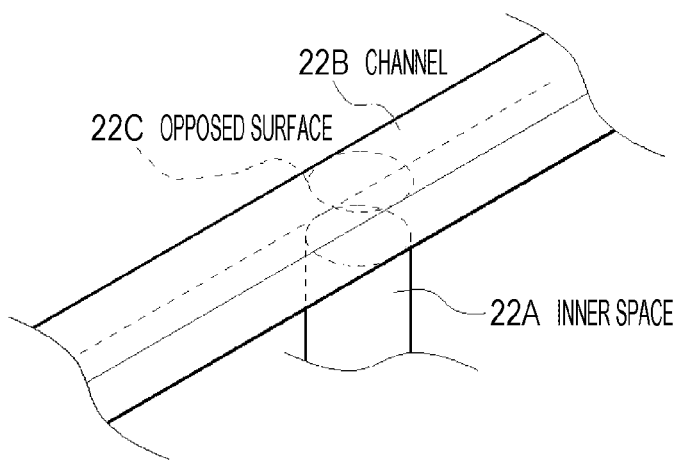
FIG. 4B is a close up view of the channel and inner space of FIG. 4A.

As illustrated in FIG. 4B, the channel 22B has a rectangular cross section whose width has the same length as that of the diameter of the inner space 22A. The height of the cross section of the channel 22B is shorter than the width of the cross section of the channel 22B. Hydrophilic processing is applied to the surfaces of the inner space 22A and the channel 22B. Examples of hydrophilic processing employed herein include plasma processing, and application of surfactant (sodium stearate). Hydrophilic processing may be applied to the tip surface (upper surface) of the piston 21.

The diameter of the inner space 22A of the cylinder unit 22 has the same length as that of the width of the channel 22B. The center position of the axis of the inner space 22A and the center position of the width of the channel 22B agree with each other.

The cover units 23 and 24 are connected with one and the other side surfaces of the cylinder unit 22 where the channel 22B is formed, respectively. The cover units 23 and 24 are connected with the side surfaces via the fixing members 29. The channels 23A and 24A are formed in the cover units 23 and 24 at such positions as to be opposed to the channel 22B of the cylinder unit 22. The channels 23A and 24A penetrate the cover units 23 and 24 in the direction along the channel 22B.

One end of the channel 23A of the cover unit 23 is connected with the channel 22B of the cylinder unit 22, while the other end of the channel 23A of the cover unit 23 is connected with the suction pipe 7A. This allows communication between the suction pipe 7A and the channel 22B.

One end of the channel 24A of the cover unit 24 is connected with the channel 22B of the cylinder unit 22, while the other end of the channel 24A of the cover unit 24 is connected with the delivery pipe 7B. This allows communication between the channel 22B and the delivery pipe 7B.

The unidirectional valve 25 of the delivery unit 8 is provided between the channel 23A of the cover unit 23 and the channel 22B of the cylinder unit 22, while the unidirectional valve 26 of the delivery unit 8 is provided between the channel 22B of the cylinder unit 22 and the channel 24A of the cover unit 24.

The unidirectional valve 25 allows flow of chemical liquid from the channel 23A of the cover unit 23 to the channel 22B of the cylinder unit 22, and does not allow flow of chemical liquid from the channel 22B of the cylinder unit 22 to the channel 23A of the cover unit 23. Examples of the unidirectional valve 25 include an umbrella valve.

The unidirectional valve 26 allows flow of chemical liquid from the channel 22B of the cylinder unit 22 to the channel 24A of the cover unit 24, and does not allow flow of chemical liquid from the channel 24A of the cover unit 24 to the channel 22B of the cylinder unit 22. Examples of the unidirectional valve 26 include an umbrella valve.

In the delivery unit 8, in delivering chemical liquid from the chemical liquid storage unit 6 into the living body, the piston 21 driven by the drive unit 9 shifts from a push-in end position (hereinafter referred to as push-end position as well) to a retraction end position (hereinafter referred to as retraction position as well) within the inner space 22A to suck the chemical liquid stored in the chemical liquid storage unit 6 into the inner space 22A.

Then, the delivery unit 8 delivers the sucked chemical liquid from the inner space 22A into the living body in accordance with the shift of the piston 21 driven by the drive unit 9 from the retraction position to the push-end position.

The delivery unit 8 can supply chemical liquid approximately in the range from 1 μL to 2 μL into the body of the user by one reciprocative action of the piston 21. The delivery unit 8 supplies a desired amount of chemical liquid to the user at a desired speed by repeating this action in cycles and at intervals established beforehand.

The push-end position is set at such a position that the tip of the piston 21 is located in the same plane as the bottom surface of the channel 22B (surface to which the inner space 22A is connected), or located at a position shifted toward the interior of the channel 22B from the position in the same plane as the bottom surface of the channel 22B. More specifically, in driving the piston 21 to the push-end position, the drive unit 9 drives the piston 21 to such a position that the tip of the piston 21 is located in the same plane as the bottom surface of the channel 22B, or located at a position shifted toward the interior of the channel 22B from the position in the same plane as the bottom surface of the channel 22B as illustrated in FIG. 5.

According to this structure, when bubbles exist in the inner space 22A, the delivery unit 8 can push out the bubbles existing in the inner space 22A into the channel 22B via the tip surface (upper surface) of the piston 21 while the piston 21 is shifting toward the push-end position. Accordingly, such a probability can considerably decrease that the bubbles again come into the inner space 22A in accordance with the shift of the piston 21 to the retraction position.

On the other hand, in the case of a device which does not shift the tip of the piston to the interior of the channel, it may occur that bubbles existing in the inner space while adhering to the side surface of the cylinder unit contacting the inner space or adhering to the tip surface of the piston are not pushed out into the channel in accordance with the sliding of the piston, for example.

In this case, the bubbles repeatedly expand and contract by a change of the inside pressure variable in accordance with the shift of the piston. As a result, the amount of chemical liquid to be sucked into the inner space varies, wherefore a predetermined amount of chemical liquid is difficult to be delivered into the living body. Accordingly, accurate supply of chemical liquid may be difficult when this type of device is used.

On the other hand, the chemical liquid supplying device 1 pushes out bubbles existing in the inner space 22A into the channel 22B in accordance with the shift of the piston 21 to the push-end position in the delivery unit 8. In this case, only chemical liquid is allowed to be sucked into the inner space 22A at the subsequent shift of the piston 21 to the retraction position. Accordingly, the chemical liquid supplying device 1 achieves accurate supply of chemical liquid.

Moreover, according to the chemical liquid supplying device 1, hydrophilic processing is applied to the tip surface of the piston 21, and the surfaces of the inner space 22A and the channel 22B. Accordingly, stay of bubbles in the inner space 22A and the channel 22B can be more securely prevented.

Structure of Drive Unit

As illustrated in FIGS. 6A-6B, the drive unit 9 includes a base unit 31, a motor 32, a motor support unit 34, a motor fixing plate 35, a fixing plate support unit 36, a bearing unit 37, a coupling 38, and a bearing support unit 39.

The respective components of the drive unit 9 are disposed on the base unit 31. The motor 32 is fixed to the base unit 31 while sandwiched between the motor support unit 34 and the motor fixing plate 35 supported by the fixing plate support unit 36.

A motor shaft 33 of the motor 32 projects from the side surface of the motor 32 on the motor fixing plate 35 side. Screw grooves 33A are formed on the side surface of the motor shaft 33.

The bearing unit 37 is a hollow unit having a substantially rectangular parallelepiped long and narrow shape extending in the axial direction of the motor 32. A screw hole 37A is formed at the center of the side surface corresponding to the short side of the substantially rectangular parallelepiped shape of the bearing unit 37. The motor shaft 33 of the motor 32 penetrates through the screw hole 37A and engages with the screw grooves 33A.

The piston 21 is connected with the bearing unit 37 via the coupling 38 in such a position as to be coaxial with the motor shaft 33. The piston 21 is connected with the side surface corresponding to the short side of the substantially parallelepiped shape of the bearing unit 37 and located on the side opposed to the side surface where the screw hole 37A is formed. The bearing unit 37 is supported by the bearing support unit 39. Examples of the coupling 38 include a part which buffers deviation of the axial direction between the motor shaft 33 and the piston 21.

Figure 7:
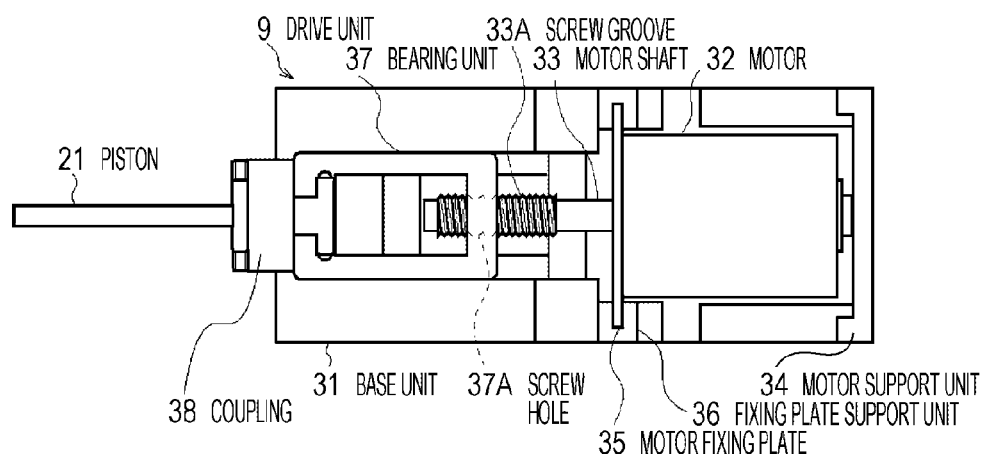
FIG. 7 is a diagram schematically illustrating the structure of the drive unit.

As illustrated in FIGS. 6A-6B and FIG. 7, the motor shaft 33 of the drive unit 9 rotates by the drive of the motor 32, and the bearing unit 37 engaging with the motor shaft 33 shifts in the axial direction in accordance with the rotation of the motor shaft 33 and reciprocates the piston 21 in the axial direction. The drive unit 9 thus constructed allows the piston 21 to slide within the inner space 22A of the cylinder unit 22. FIGS. 6A-6B show the piston 21 located at the retraction position, while FIG. 7 shows the piston 21 located at the push-end position.

According to the drive unit 9, the motor shaft 33 of the motor 32 is positioned coaxially with the piston 21. This equalizes the direction of a force applied to the bearing unit 37 in accordance with the rotation of the motor shaft 33, and the direction of a force applied to the piston 21 generated by the force applied to the bearing unit 37. In this case, thrust loss of the piston 21 is not produced.

Accordingly, the drive unit 9 allows the piston 21 to slide with a stable stroke distance within the inner space 22A of the cylinder unit 22. Moreover, without thrust loss of the piston 21, the drive unit 9 can drive the piston 21 by a smaller force. Accordingly, the motor 32, a battery and the like can be miniaturized, wherefore the entire device can be made compact. For reduction of sliding resistance, the side surface of the piston 21 may be coated with diamond-like carbon.

On the other hand, in case of a device which does not coaxially position the piston and the shaft of the motor, the force applied to the bearing unit by rotation of the shaft is offset from the force applied to the piston by the force applied to the bearing unit. In this case, thrust loss of the piston increases, and the sliding resistance generated on the bearing unit and the piston rises due to the offset of the forces. This condition not only produces unstable strokes of the piston, but also increases the entire size of the device.

Figure 8A:
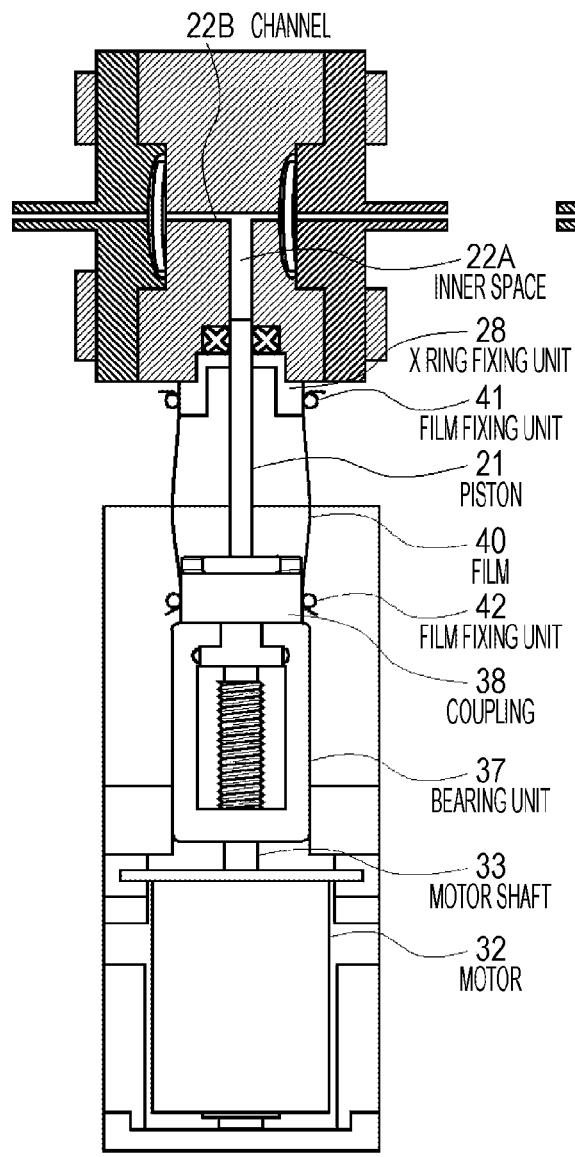
FIG. 8A is a diagram schematically illustrating the structures of the delivery unit including a film, and the drive unit when the piston is back.
Figure 8B:
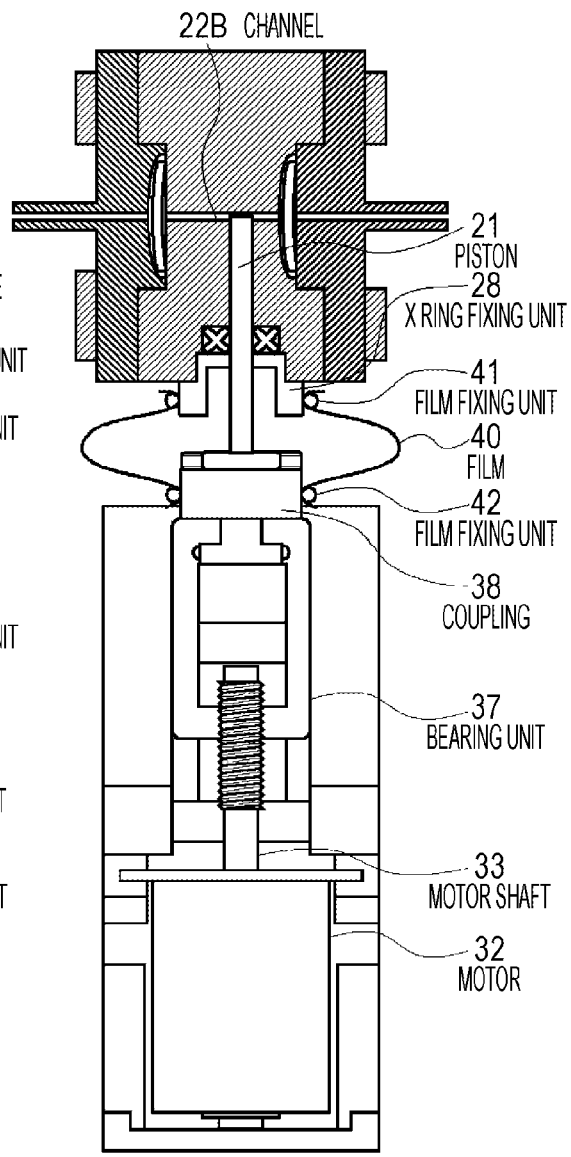
FIG. 8B is a diagram schematically illustrating the structures of the delivery unit including a film, and the drive unit when the piston is forward.

As illustrated in FIGS. 8A-8B, the portion of the chemical liquid supplying device 1 between the X ring fixing unit 28 and the coupling 38 is covered with a tube-shaped flexible film 40. Examples of the material of the film 40 include polyethylene.

The film 40 is fixed to the X ring fixing unit 28 and the coupling 38 without clearances between the film 40 and the X ring fixing unit 28 and the coupling 38 in the circumferential direction. This fixation of the film 40 is made by film fixing units 41 and 42 constituted by O rings, for example, fixed to both ends of the film 40.

The film 40 has flexibility, and therefore constantly secures the condition covering the piston 21 from the state of the retraction position of the piston 21 as illustrated in FIG. 8A to the state of the push-end position of the piston 21 as illustrated in FIG. 8B.

Accordingly, the chemical liquid supplying device 1 allows sliding of the piston 21 within the inner space 22A of the cylinder unit 22 without exposing the piston 21 to the air outside the film 40. Accordingly, the chemical liquid supplying device 1 can more securely maintain the cleanliness of the piston 21 to be inserted into the inner space 22A.

Structure of Puncture Mechanism

Figure 9:
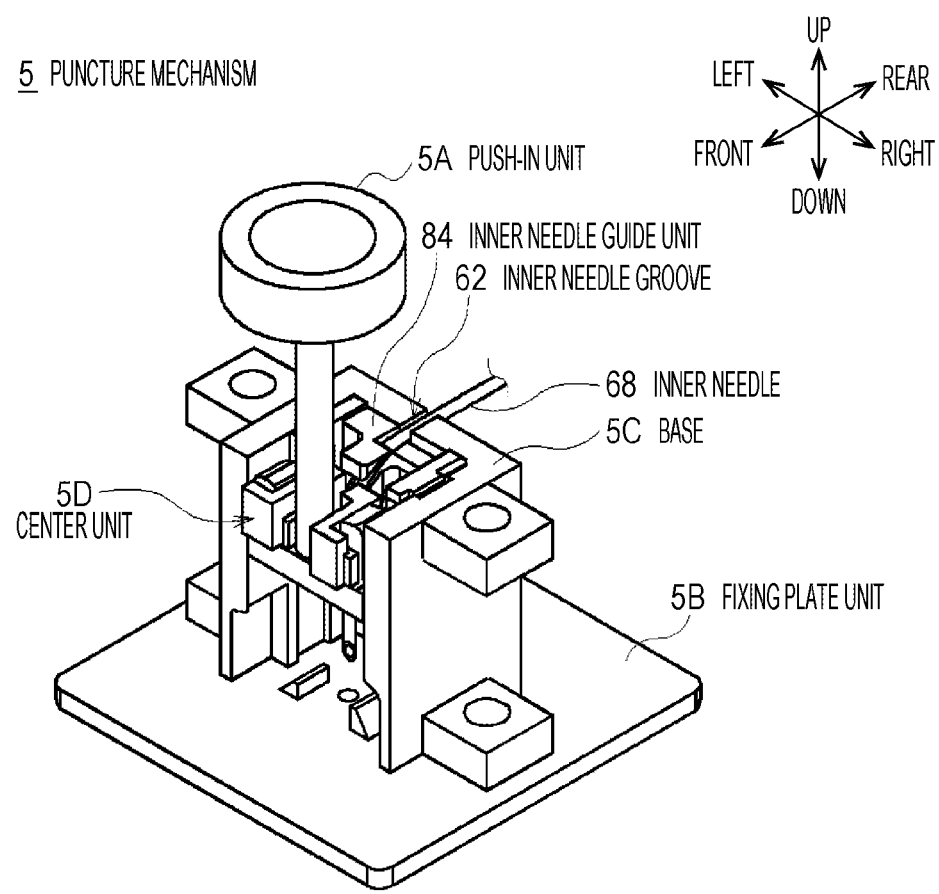
FIG. 9 is a diagram schematically illustrating the structure of a puncture mechanism.
Figure 11:
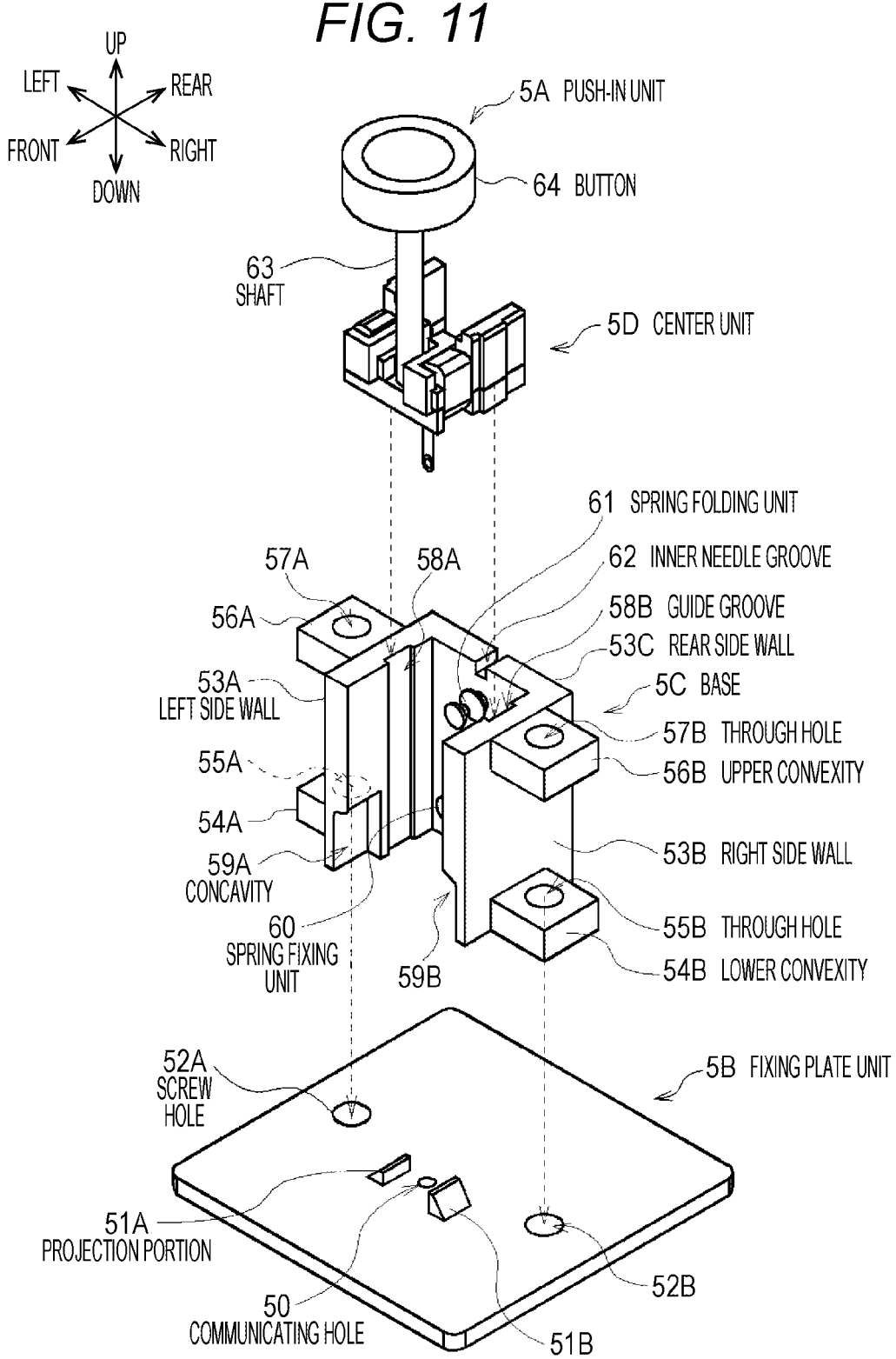
FIG. 11 is a diagram schematically illustrating the structure of the puncture mechanism.

The structure of the puncture mechanism 5 is now detailed. As illustrated in FIGS. 9-11, the puncture mechanism 5 chiefly includes the push-in unit 5A, a fixing plate unit 5B fixed to the inside of the front end of the bottom surface 2A of the lower housing unit 2, a base 5C projecting from the fixing plate unit 5B, and a center unit 5D capable of sliding in the up-down direction inside the base 5C in accordance with push-in operation of the push-in unit 5A.

An inner needle groove 62, an inner needle 68, and an inner needle guide unit 84 illustrated in FIG. 9 will be described later.

As illustrated in FIG. 11, the fixing plate unit 5B has a substantially square plate shape. A communicating hole 50 is provided at the center of the fixing plate unit 5B. The communicating hole 50 communicates with the puncture needle hole 2B formed on the bottom surface 2A of the lower housing unit 2. Two projection portions 51A and 51B further project from the left side and the right side of the communicating hole 50, respectively, with a predetermined space left between the two projection portions 51A and 51B.

Screw holes 52A and 52B are further formed at predetermined positions outside the two projection portions 51A and 51B. The screw holes 52A and 52B correspond to the attachment position of the base 5C.

The base 5C has a shape having a U-shaped cross section and including three walls 53A, 53B, and 53C on the left and right sides and the rear side. Lower convexities 54A and 54B projecting to the outside are formed at the lower ends of the outer surfaces of the left side wall 53A and the right side wall 53B, respectively.

Through holes 55A and 55B are formed in the lower convexities 54A and 54B, respectively, and penetrate the lower convexities 54A and 54B in the up-down direction.

The base 5C is fixed to a predetermined position of the fixing plate unit 5B by placing the two through holes 55A and 55B immediately above the screw holes 52A and 52B of the fixing plate unit 5B, and fitting screws (not shown) into the screw holes 52A and 52B of the fixing plate unit 5B via the through holes 55A and 55B.

Moreover, upper convexities 56A and 56B projecting to the outside are formed at the upper ends of the outer surfaces of the left side wall 53A and the right side wall 53B. The upper convexities 56A and 56B similarly have through holes 57A and 57B, respectively. The through holes 57A and 57B are holes through which screws are fixed to the base 5C to a predetermined position of the upper housing unit 3.

Furthermore, grooves 58A and 58B are formed on the inner surfaces of the left side wall 53A and the right side wall 53B, respectively. The grooves 58A and 58B are offset toward the rear and extend from the lower ends of the left side wall 53A and the right side wall 53B toward the upper ends thereof. The grooves 58A and 58B correspond to grooves for guiding the center unit 5D sliding along the inner wall of the base 5C. The grooves 58A and 58B are hereinafter referred to as guide grooves 58A and 58B.

Furthermore, concavities 59A and 59B are formed on the inner side surfaces of the left side wall 53A and the right side wall 53B, respectively. The concavities 59A and 59B are disposed at the lower ends of the left side wall 53A and the right side wall 53B and offset toward the front. The functions of the concavities 59A and 59B will be described later.

Furthermore, a spring fixing unit 60 for fixing one end of a coil spring (described later) projects from the inner surface of the rear side wall 53C. The spring fixing unit 60 is disposed at a position at the lower end of the rear side wall 53C and offset toward the left.

Furthermore, a spring folding unit 61 projects from the inner surface of the rear side wall 53C. The spring folding unit 61 is disposed at a position at the center of the rear side wall 53C and offset upward, and folds the other end of the coil spring (not shown) whose one end is fixed to the spring fixing unit 60. The coil spring will be detailed later. The coil spring has the function of retracting only an outer needle into the chemical liquid supplying device 1 after insertion of a puncture needle containing a metal outer needle and a resin inner needle into the body of the user.

Furthermore, an inner needle groove 62 through which the inner needle is inserted is formed at the center of the upper surface of the rear side wall 53C.

The center unit 5D is partly fixed to the lower end of a shaft 63 of the push-in unit 5A. The center unit 5D slides inside the base 5C in accordance with the push-in operation of the push-in unit 5A. A button 64 whose shape is easily pushed in with a finger (such as a disk-like shape in the same size as the size of the finger cushion) is provided at the upper end of the shaft 63 of the push-in unit 5A.

Figure 12:
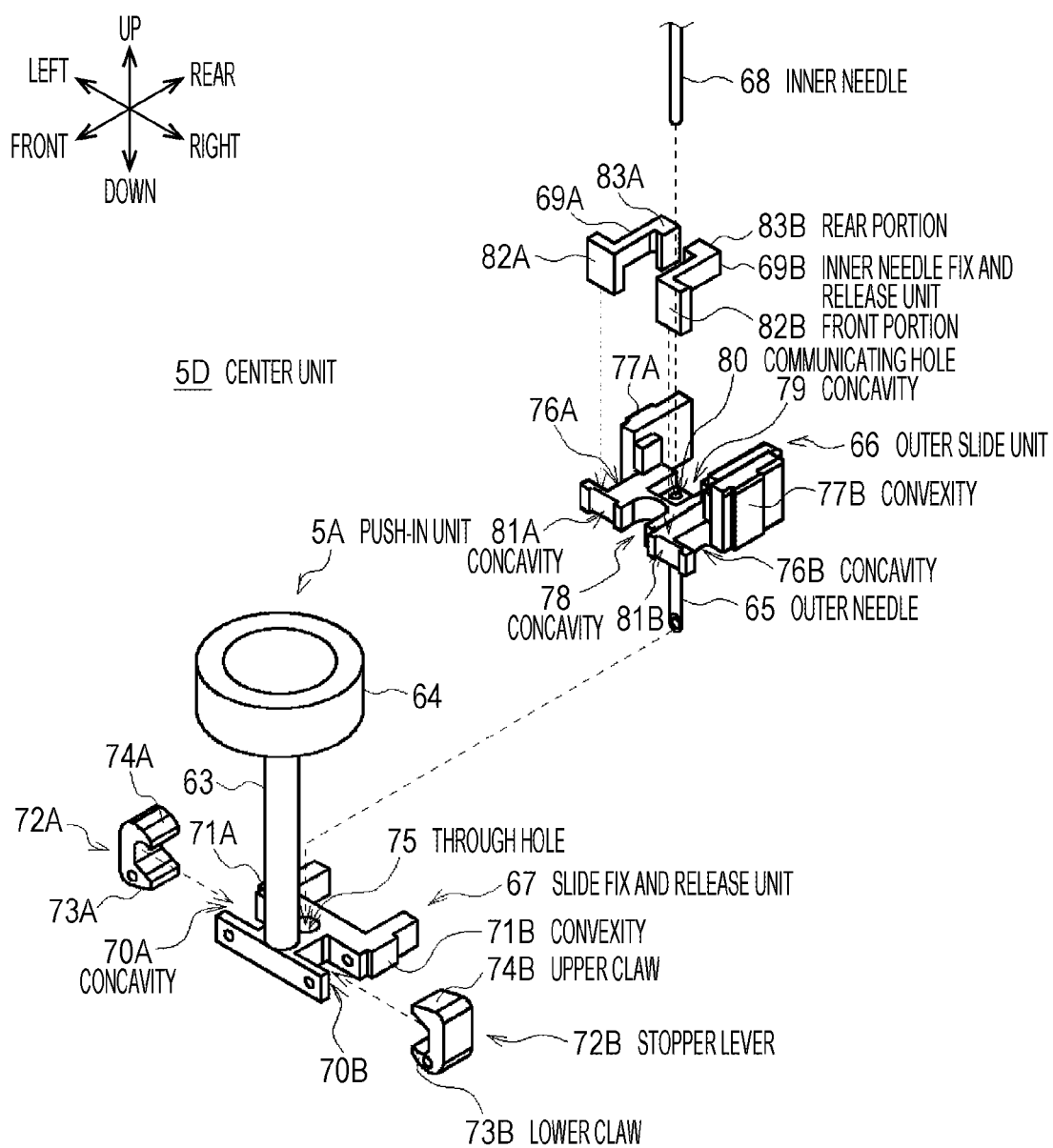
FIG. 12 is a diagram schematically illustrating the structure of a center unit.

The center unit 5D is now described in more detail. As illustrated in FIG. 12, the center unit 5D chiefly includes an outer needle slide unit 66 having an outer needle 65 of the puncture needle, a slide fix and release unit 67 fastened to the shaft 63 of the push-in unit 5A to fix or release the outer needle slide unit 66, and a pair of inner needle fix and release units 69A and 69B for fixing or releasing the inner needle 68 of the puncture needle.

The slide fix and release unit 67 has a substantially U-shaped plate shape which has a substantially T-shape on the front side, and is opened to the rear on the rear side, the shaft 63 of the push-in unit 5A is attached to the center of the front end of the slide fix and release unit 67.

The slide fix and release unit 67 further includes concavities 70A and 70B. The concavities 70A and 70B are formed on the left and right side surfaces of the slide fix and release unit 67, respectively, and disposed at positions offset toward the front. On the other hand, convexities 71A and 71B are formed on the left and right side surfaces of the slide fix and release unit 67, respectively, and disposed at positions offset toward the rear.

The left and right convexities 71A and 71B are portions fitted to the guide grooves 58A and 58B of the base 5C, respectively. This allows the slide fix and release unit 67 to slide in the up-down direction along the guide grooves 58A and 58B of the base 5C.

Moreover, stopper levers 72A and 72B each having a U-shaped cross section are rotatably supported on the left and right concavities 70A and 70B, respectively, in such positions that openings of the stopper levers 72A and 72B face to each other.

More specifically, lower claws 73A and 73B of the stopper levers 72A and 72B are supported by the concavities 70A and 70B, respectively, via rotation shafts (not shown) extending in the front-rear direction.

This allows the stopper levers 72A and 72B to rotate around axes corresponding to the lower claws 73A and 73B, in such directions that upper claws 74A and 74B move close to each other and move away from each other.

It is assumed herein that rotation of the upper claws 74A and 74B in such directions that upper claws 74A and 74B move close to each other corresponds to closing of the stopper levers 72A and 72B, and that rotation of the upper claws 74A and 74B in such directions that upper claws 74A and 74B move away from each other corresponds to opening of the stopper levers 72A and 72B.

When the stopper levers 72A and 72B are closed, the upper claws 74A and 74B are configured to be positioned above the upper surface of the slide fix and release unit 67 by a predetermined length.

Moreover, when the stopper levers 72A and 72B are closed, the stopper levers 72A and 72B are configured to be accommodated within the slide fix and release unit 67 without producing projections from the left and right side surfaces of the slide fix and release unit 67. In other words, when the stopper levers 72A and 72B are closed, the slide fix and release unit 67 is in such a condition that only the convexities 71A and 71B project from the left and right side surfaces of the slide fix and release unit 67.

Furthermore, the slide fix and release unit 67 has a through hole 75 for passing the outer needle 65 which penetrates the center of the slide fix and release unit 67 in the up-down direction.

The outer needle slide unit 66 is configured to overlap on the slide fix and release unit 67. The outer needle slide unit 66 is a substantially U-shaped unit which has a substantially T-shape on the front side, and is opened to the rear on the rear side. The substantially T-shaped portion on the front side is a plate-shaped, while the left and right side surfaces on the rear side extend upward for each.

Concavities 76A and 76B are formed on the left and right side surfaces of the outer needle slide unit 66, respectively, at positions offset toward the front. In addition, convexities 77A and 77B are formed on the left and right side surfaces of the outer needle slide unit 66, respectively, at positions offset toward the rear.

The convexities 77A and 77B are portions fitted to the guide grooves 58A and 58B of the base 5C, respectively. This allows the outer needle slide unit 66 to slide in the up-down direction along the guide grooves 58A and 58B of the base 5C.

A concavity 78 is formed at the center of the front end of the outer needle slide unit 66 so as to avoid interference between the outer needle slide unit 66 and the shaft 63 of the push-in unit 5A when the outer needle slide unit 66 is overlapped on the slide fix and release unit 67.

Moreover, the metal outer needle 65 projects downward from the center of the bottom surface of the outer needle slide unit 66. The outer needle 65 is a hollow pipe-shaped needle, and has a length of 8 mm, an outside diameter of 0.4 mm, and an inside diameter of 0.2 mm, for example.

Furthermore, a concavity 79 is formed at the center of the upper surface of the outer needle slide unit 66. A communicating hole 80 is formed at the center of the concavity 79. The communicating hole 80 communicates with the outer needle 65 provided on the bottom surface of the outer needle slide unit 66. The inner needle 68 having an outside diameter smaller than the inside diameter of the outer needle 65 is inserted into the communicating hole 80 so as to be inserted into the outer needle 65.

Furthermore, concavities 81A and 81B each having a smaller depth than the depth of the concavity 78 are formed on the front surface of the outer needle slide unit 66 on the left and right sides of the concavity 78.

The external shape of the bottom surface of the outer needle slide unit 66 has substantially the same shape and the same size as those of the upper surface of the slide fix and release unit 67 except for the concavities 78, 81A and 81B at the front end of the outer needle slide unit 66.

This allows connection between the convexities 77A and 77B formed on the left and right side surfaces of the outer needle slide unit 66 and the convexities 71A and 71B formed on the left and right side surfaces of the slide fix and release unit 67 without producing steps when the outer needle slide unit 66 is overlapped on the slide fix and release unit 67 in such a manner as to allow insertion of the outer needle 65 into the through hole 75 of the slide fix and release unit 67.

The inner needle fix and release units 69A and 69B are made of an elastic member, and are symmetric in the left-right direction. Front portions 82A and 82B formed on the inner needle fix and release units 69A and 69B, respectively, project toward the outside, and rear portions 83A and 83B formed on the inner needle fix and release units 69A and 69B, respectively, project toward the inside. Accordingly, each of the inner needle fix and release units 69A and 69B has a substantially Z-shape.

Moreover, the front portions 82A and 82B of the inner needle fix and release units 69A and 69B project downward. Similarly, the rear portions 83A and 83B of the inner needle fix and release units 69A and 69B project downward.

The front portions 82A and 82B of the inner needle fix and release units 69A and 69B are fitted to the left and right concavities 81A and 81B formed on the front surface of the outer needle slide unit 66. The rear portions 83A and 83B of the inner needle fix and release units 69A and 69B are inserted into the concavity 79 formed at the center of the upper surface of the outer needle slide unit 66. In this condition, the inner needle fix and release units 69A and 69B are held on the outer needle slide unit 66 in such positions as to face to each other.

In this case, the rear portions 83A and 83B of the inner needle fix and release units 69A and 69B are opposed to each other while leaving a clearance between each other, which clearance is longer than the outside diameter of the inner needle 68. In this arrangement, the inner needle 68 to be inserted into the outer needle 65 of the outer needle slide unit 66 is positioned between the rear portions 83A and 83B.

Figure 13:
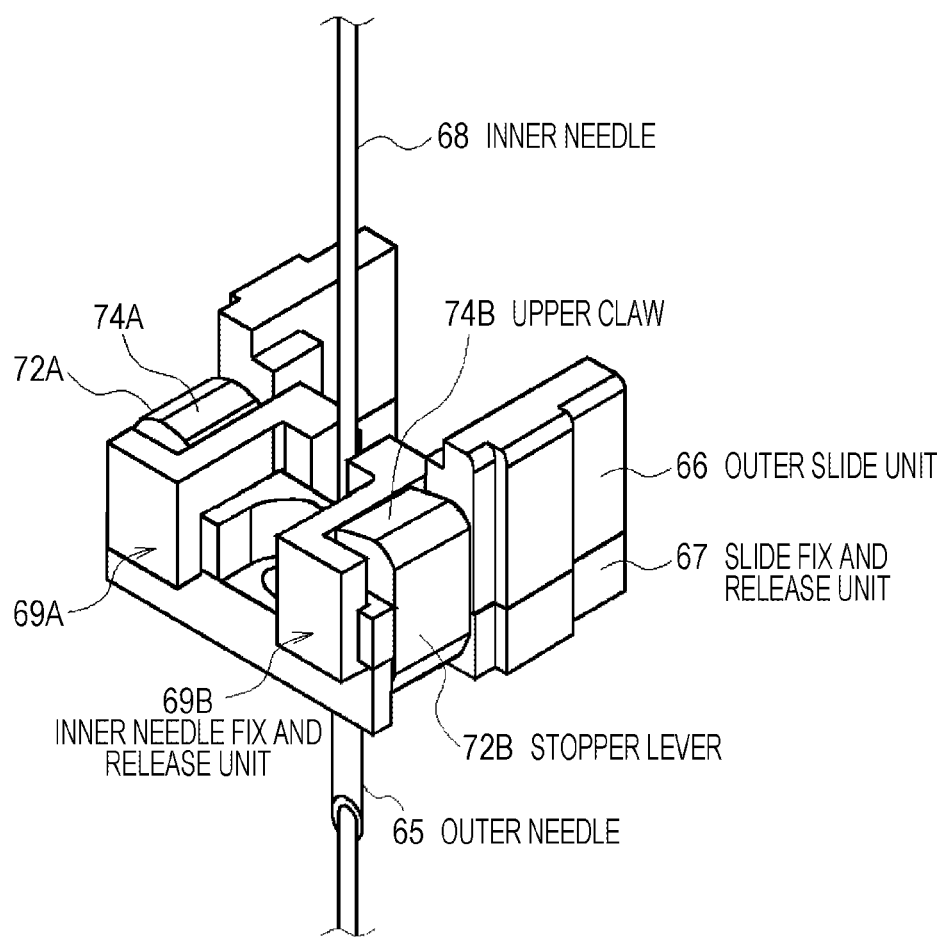
FIG. 13 is a diagram schematically illustrating the center unit with stopper levers closed.

Suppose that the left and right stopper levers 72A and 72B of the slide fix and release unit 67 are closed with the outer needle slide unit 66 overlapped on the slide fix and release unit 67, with the inner needle 68 inserted into the outer needle 65 of the outer needle slide unit 66, and with the inner needle fix and release units 69A and 69B disposed on the outer needle slide unit 66 as illustrated in FIG. 13.

In this condition, the outer needle slide unit 66 is fixed to the slide fix and release unit 67 by insertion of the outer needle slide unit 66 between the upper claws 74A and 74B of the left and right stopper levers 72A and 72B and the upper surface of the slide fix and release unit 67.

In addition, under this condition, the upper claws 74A and 74B of the left and right stopper levers 72A and 72B press the outer surfaces of the left and right inner needle fix and release units 69A and 69B toward the inside, respectively.

Figure 14B:
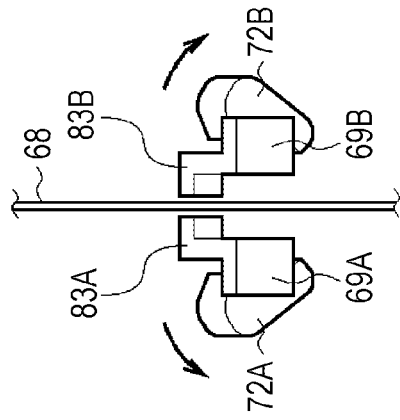
FIG. 14B is a diagram schematically illustrating release of fixation of an inner needle by operations of an inner needle fix and release unit and the stopper levers.
Figure 14A:
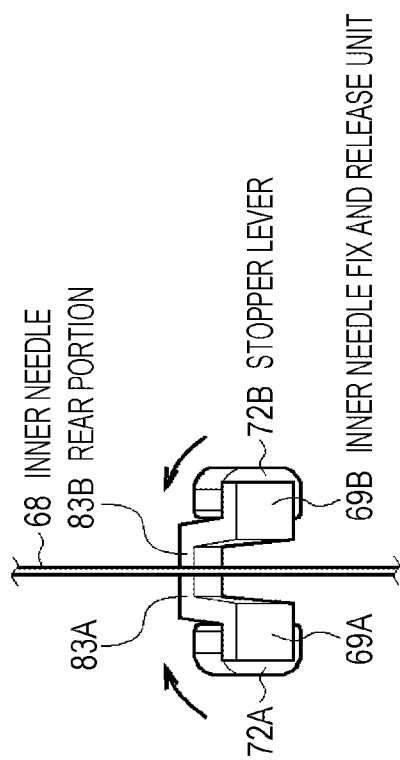
FIG. 14A is a diagram schematically illustrating fixation of an inner needle by operations of an inner needle fix and release unit and the stopper levers.

In this case, the inner needle fix and release units 69A and 69B deform in such a manner as to decrease the clearance between the rear portions 83A and 83B of the inner needle fix and release units 69A and 69B as illustrated in FIG. 14A. As a result, the inner needle 68 positioned between the rear portions 83A and 83B of the inner needle fix and release units 69A and 69B is pressed by the rear portions 83A and 83B from the left and right sides and fixed to the inner needle fix and release units 69A and 69B.

The inner needle fix and release units 69A and 69B are held by the outer needle slide unit 66. Accordingly, fixation of the inner needle 68 to the inner needle fix and release units 69A and 69B coincides with fixation of the inner needle 68 to the outer needle slide unit 66.

On the other hand, suppose that the left and right stopper levers 72A and 72B are opened in this condition. In this case, the fixation of the outer needle slide unit 66 to the slide fix and release unit 67 is released. In addition, the inner needle fix and release units 69A and 69B in this state are deformed in such a manner as to restore the clearance between the rear portions 83A and 83B to the original clearance as illustrated in FIG. 14B. As a result, the fixation of the inner needle 68 to the inner needle fix and release units 69A and 69B is also released.

The center unit 5D thus constructed is fitted to the inside of the base 5C in such a manner as to freely slide by fitting the convexities 71A and 71B of the slide fix and release unit 67 and the convexities 77A and 77B of the outer needle slide unit 66 to the guide grooves 58A and 58B inside the base 5C with the outer needle slide unit 66 overlapped on the slide fix and release unit 67, with the inner needle 68 inserted into the outer needle 65 of the outer needle slide unit 66, and with the inner needle fix and release units 69A and 69B disposed on the outer needle slide unit 66.

As illustrated in FIG. 9, the inner needle 68 is inserted from the rear side of the puncture mechanism 5, and passes through the inner needle groove 62 formed at the center of the upper surface of the rear side wall 53C of the base 5C. Then, the inner needle 68 is bended downward by the inner needle guide unit 84 fixed to the inside upper end of the rear side wall 53C, and is inserted into the outer needle 65 of the outer needle slide unit 66.

As illustrated in FIG. 15A, the center unit 5D is disposed in the upper area inside of the base 5C as an initial position. In this state, the entire outer needle 65 is accommodated within the chemical liquid supplying device 1, while the projection of the push-in unit 5A from the chemical liquid supplying device 1 becomes the maximum.

In addition, the left and right stopper levers 72A and 72B of the center unit 5D in this state are in the closed condition while pressed toward the inside by the left side wall 53A and the right side wall 53B of the base 5C.

In other words, the center unit 5D in this state fixes the outer needle slide unit 66 to the slide fix and release unit 67, and fixes the inner needle 68 to the outer needle slide unit 66 via the inner needle fix and release units 69A and 69B.

In addition, at this initial position, the center unit 5D is located before the spring folding unit 61 disposed at a position at the center of the rear side wall 53C of the base 5C and offset upward as illustrated FIG. 15E.

Figure 16A:
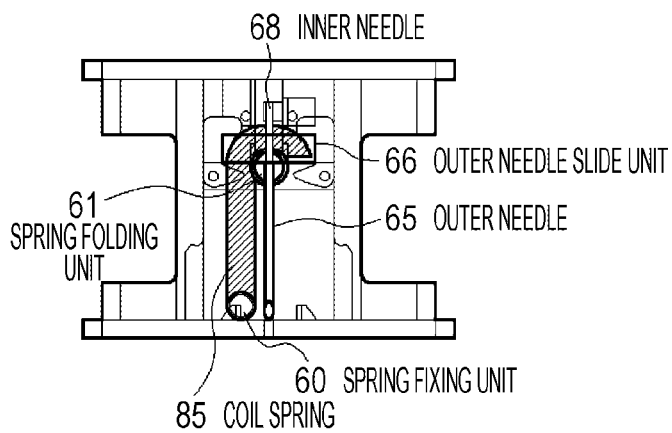
FIG. 16A is a diagram schematically describing retraction of an outer needle by operation of a coil spring in an initial position.

In this case, one end of a coil spring 85 is fixed to the spring fixing unit 60 disposed at a position at the lower end of the rear side wall 53C of the base 5C and offset toward the left, while the other end of the coil spring 85 is bended downward by the spring folding unit 61 in a J-shape as illustrated in FIG. 16A. In this condition, the other end of the coil spring 85 is fixed to a predetermined position disposed behind the outer needle slide unit 66 and offset toward the right. FIGS. 16A-16D do not show a part of the puncture mechanism 5, and contain deformed shapes of the outer needle slide unit 66 for convenience of explanation.

Figure 16B:
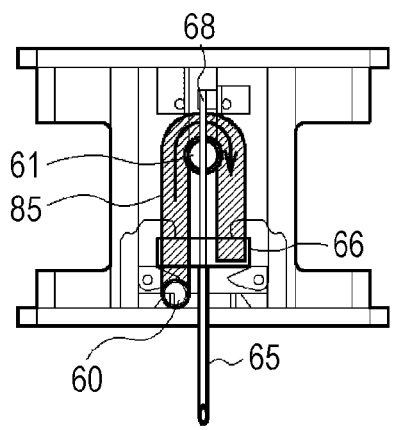
FIG. 16B is a diagram schematically describing retraction of an outer needle by operation of a coil spring in a position after the push-in button has been pressed.

The coil spring 85 in this state has a natural length without expansion and contraction. When the user pushes the push-in unit 5A into the chemical liquid supplying device 1 in this condition, the center unit 5D slides downward inside the base 5C as illustrated in FIG. 16B. In accordance with this downward sliding of the outer needle slide unit 66 of the center unit 5D, the entire coil spring 85 expands with deformation from the J-shape into a U-shape.

Operation of Puncture Mechanism

The actual operation of the puncture mechanism 5 at the time of insertion of the outer needle 65 and the inner needle 68 of the puncture needle into the body of the user is now described in detail.

As illustrated in FIG. 15A, the center unit 5D of the puncture mechanism 5 is initially set at the initial position. In this condition, the entire outer needle 65 is accommodated in the chemical liquid supplying device 1, while the projection of the push-in unit 5A from the chemical liquid supplying device 1 becomes the maximum.

In this state, the left and right stopper levers 72A and 72B of the center unit 5D are closed as discussed above, and fix the outer needle slide unit 66 to the slide fix and release unit 67 and also fix the inner needle 68 to the outer needle slide unit 66 via the inner needle fix and release units 69A and 69B.

In this state, the inner needle 68 is retained inside the outer needle 65 in such a condition as to maintain the position of the tip of the inner needle 68 substantially at the same position as the position of the tip of the outer needle 65 without projection from the tip of the outer needle 65 as illustrated in FIG. 17A.

Then, the user attaches the chemical liquid supplying device 1 to a predetermined position of the body, and pushes the push-in unit 5A into the chemical liquid supplying device 1.

As a result, the center unit 5D of the puncture mechanism 5 slides downward inside the base 5C, and the coil spring 85 expands with the other end of the coil spring 85 fixed to the outer needle slide unit 66 of the center unit 5D as illustrated in FIGS. 15B and 16B.

In this state, the outer needle 65 of the center unit 5D slides downward while holding the inner needle 68 inside, passes through the communicating hole 50 of the fixing plate unit 5B, and projects from the puncture needle hole 2B to be inserted into the body of the user together with the inner needle 68.

Figure 16C:
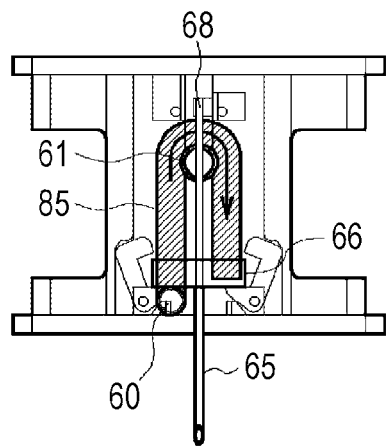
FIG. 16C is a diagram schematically describing retraction of an outer needle by operation of a coil spring in a position just after the outer needle has been released.

When the push-in unit 5A is further pushed in, the entire shaft 63 of the push-in unit 5A is accommodated within the chemical liquid supplying device 1 as illustrated in FIGS. 15C and 16C. In this state, the projecting portion of the push-in unit 5A from the chemical liquid supplying device 1 corresponds to only the button 64, wherefore the projection becomes the minimum.

When the push-in unit 5A is completely pushed in as in this manner, the center unit 5D in this state reaches the lower end of the base 5C. Under this condition, the outer needle 65 and the inner needle 68 of the puncture needle are inserted most deeply within the body of the user as illustrated in FIG. 17B. The chemical liquid supplying device 1 is designed such that the length of the portion to be inserted into the body of the user becomes 7 mm, for example.

In addition, the concavities 59A and 59B formed at the lower ends of the left side wall 53A and the right side wall 53B in this state are located outside the stopper levers 72A and 72B of the center unit 5D. Accordingly, the stopper levers 72A and 72B are not pressed toward the inside, and therefore come into an openable condition.

In this state, the two projection portions 51A and 51B provided on the fixing plate unit 5B contact the tips of the lower claws 73A and 73B of the stopper levers 72A and 72B, and push up the tips of the lower claws 73A and 73B. As a result, the stopper levers 72A and 72B rotate toward the outside and open.

Accordingly, the fixation between the slide fix and release unit 67 and the outer needle slide unit 66 of the center unit 5D is released. Simultaneously, the fixation between the outer needle slide unit 66 and the inner needle 68 via the inner needle fix and release units 69A and 69B is released.

In other words, the two projection portions 51A and 51B of the fixing plate unit 5B function as a release unit which contacts the stopper levers 72A and 72B to release the fixation between the slide fix and release unit 67 and the outer needle slide unit 66, and the fixation between the outer needle slide unit 66 and the inner needle 68, which fixations have been made by the stopper levers 72A and 72B.

Figure 16D:
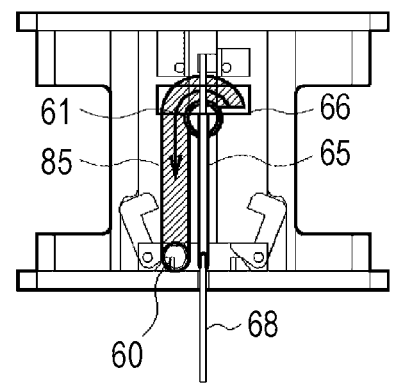
FIG. 16D is a diagram schematically describing retraction of an outer needle by operation of a coil spring in a position after the coil has retracted.

When these fixations are released in this manner, the outer needle slide unit 66 slides upward together with the inner needle fix and release units 69A and 69B, and returns to the original position by the restoring force of the coil spring 85 as illustrated in FIGS. 15D and 16D.

As a result, the entire outer needle 65 is removed from the inside of the body of the user, and accommodated within the chemical liquid supplying device 1. In this state, the inner needle 68 is not fixed to the outer needle slide unit 66 after release of the fixation by the inner needle fix and release units 69A and 69B. Thus, the inner needle 68 remains within the body of the user and indwells therein as illustrated in FIG. 17C.

Accordingly, the puncture mechanism 5 inserts the inner needle 68 together with the outer needle 65 into the body of the user in accordance with the push-in operation of the push-in unit 5A. When the push-in unit 5A is pushed in until arrival of the center unit 5D at the lower end of the base 5C, that is, when the push-in unit 5A is completely pushed in, only the outer needle 65 is retracted with the inner needle 68 indwelled in the body.

When the push-in unit 5A of the chemical liquid supplying device 1 is completely pushed in, the button 64 of the push-in unit 5A becomes a cover of the upper housing unit 3. Moreover, sealing (not shown) is provided around the shaft 63 of the push-in unit 5A. This prevents entrance of water into the chemical liquid supplying device 1.

As discussed above, the center unit 5D of the puncture mechanism 5 of the chemical liquid supplying device 1 slides downward when the push-in unit 5A is pushed in by the user. In accordance with this sliding, the outer needle 65 containing the inner needle 68 inside is inserted into the body of the user.

When the push-in unit 5A of the chemical liquid supplying device 1 is completely pushed in, the stopper levers 72A and 72B of the center unit 5D are opened, and only the outer needle slide unit 66 of the center unit 5D is returned to the original position by the restoring force of the coil spring 85. Accordingly, only the outer needle 65 is retracted into the chemical liquid supplying device 1 with the inner needle 68 indwelled within the body of the user.

Then, the chemical liquid supplying device 1 supplies chemical liquid from the chemical liquid storage unit 6 storing the chemical liquid into the body of the user via the inner needle 68 by operation of the delivery unit 8.

Accordingly, the indwelled needle of the chemical liquid supplying device 1 is the inner needle 68 of the double-structure puncture needle. In this case, the diameter of the indwelled needle can be easily made smaller in comparison with the conventional puncture needle whose indwelled needle is the outer needle 65.

More specifically, the chemical liquid supplying device 1 can reduce the thickness of the inner needle 68 functioning as the indwelled needle and corresponding to the portion indwelled within the body of the user. Accordingly, the burden imposed on the user can decrease.

It should be noted that the inner needle 68 made of resin material may be produced as a thin-wall pipe. Thus, the inside diameter of the inner needle 68 can be made larger than the inside diameter of a metal needle when the outside diameters of the two needles are the same.

Moreover, the chemical liquid supplying device 1 can perform the processes from insertion of the puncture needle (outer needle 65 and inner needle 68) to retraction of the outer needle 65 at a time only by the push-in operation of the push-in unit 5A.

Furthermore, the puncture mechanism 5 of the chemical liquid supplying device 1 operates only by the push-in operation executed by the user. In this case, the necessity of a drive unit such as a motor for the puncture mechanism 5 is eliminated, wherefore size reduction of the puncture mechanism 5 is easily achieved. Accordingly, the space occupied by the puncture mechanism 5 inside the chemical liquid supplying device 1 can decrease. Furthermore, the chemical liquid supplying device 1 becomes a compact device having a smaller number of projections on the whole when the push-in unit 5A is completely pushed in. Accordingly, the portability of the chemical liquid supplying device 1 improves.

Electric Structure of Chemical Liquid Supplying Device

As illustrated in FIG. 18, the chemical liquid supplying device 1 includes the CPU (Central Processing Unit) 91, a ROM (Read Only Memory) 92, a RAM (Random Access Memory) 93, the power source unit 94, an interface unit (I/F unit) 95, a notification unit 96, and the drive unit 9. These components of the chemical liquid supplying device 1 are connected with one another via a bus 97.

The CPU 91, the ROM 92, the RAM 93, the power source unit 94, and the notification unit 96 are disposed on the substrate 10. The power source unit 94 is constituted by a battery. The notification unit 96 is constituted by a speaker.

The interface unit 95 is constituted by a button (not shown) which is disposed on the upper housing unit 3 or the lower housing unit 2, and receives commands input from the user.

The CPU 91 reads a basic program stored in the ROM 92, loads the program into the RAM 93, and implements the program to supervise and control the general operation. In addition, the CPU 91 reads various applications stored in the ROM 92, loads the applications into the RAM 93, and implements the applications to perform various processes.

At the time of supply of chemical liquid to the user, the CPU 91 loads a chemical liquid supply program into the RAM 93 and implements a chemical liquid supply process. After charge of chemical liquid from the outside into the chemical liquid storage unit 6, attachment of the attachment portion 4 to the skin of the user, and insertion of the puncture needle into the skin of the user by operation of the puncture mechanism 5, the CPU 91 sets parameters of the supply amount, supply speed and others input via the interface unit 95.

Then, the CPU 91 starts supply of chemical liquid by controlling the drive unit 9 in accordance with the set parameters.

OTHER EMBODIMENTS

Other Embodiment 1

As described herein, one embodiment of the present invention relates to the chemical liquid supplying device 1 supplying chemical liquid into the body of the user. However, other embodiments of the present invention relate to devices other than the chemical liquid supplying device 1 as long as these devices are puncture devices capable of inserting a puncture needle which has a double structure constituted by an outer needle and an inner needle.

For example, embodiments of the present invention may be related to sensor devices capable of inserting various types of sensors into the body of a user to obtain living body information.

Figure 19:
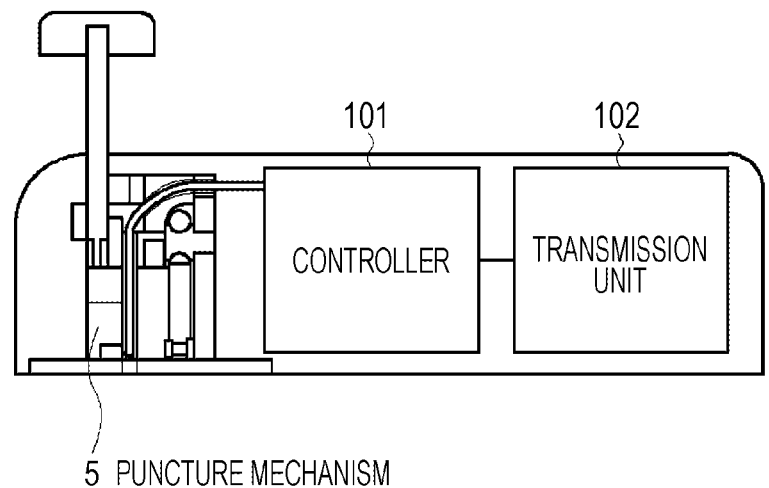
FIG. 19 is a diagram schematically illustrating the structure of a sensor device according to a different embodiment.

FIG. 19 illustrates a sensor device 100 of this type. The sensor device 100 includes the puncture mechanism 5 similar to the puncture mechanism 5 of the chemical liquid supplying device 1. However, the sensor device 100 does not have the chemical liquid storage unit 6, the delivery unit 8, and the drive unit 9, but has a controller 101 for obtaining living body information from a sensor, and a transmission unit 102 for transmitting the living body information to the outside by wireless communication.

Figure 20:
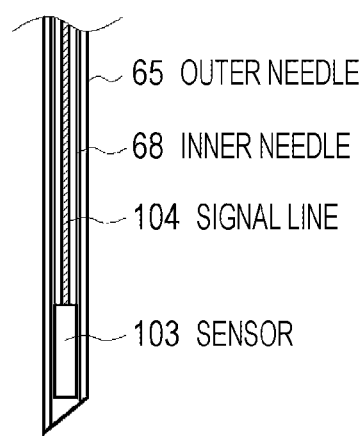
FIG. 20 is a diagram schematically illustrating the structure of a puncture needle according to the different embodiment.

As illustrated in FIG. 20, a sensor 103 is attached to the tip of the inner needle 68 of the sensor device 100. A signal line 104 for electrically connecting the sensor 103 and the controller 101 is further inserted into the inner needle 68.

According to the sensor device 100, the outer needle 65 containing the inner needle 68 inside is inserted into the body of the user by operation of the puncture mechanism 5. The sensor 103 is attached to the tip of the inner needle 68.

Then, the sensor device 100 retracts only the outer needle 65 into the sensor device 100 with the sensor 103 indwelled within the body of the user.

Thereafter, the controller 101 of the sensor device 100 obtains living body information from the sensor 103, and transmits the living body information to the outside via the transmission unit 102 by wireless communication.

Other Embodiment 2

According to the foregoing embodiments, the puncture needle (outer needle 65 and inner needle 68) is inserted into the body of the user, and only the outer needle 65 is retracted by operation of the puncture mechanism 5 illustrated in FIGS. 9-12. However, the insertion of the puncture needle and the retraction of the outer needle may be performed by using a puncture mechanism other than the puncture mechanism 5 illustrated in FIGS. 9-12.

Figure 21:
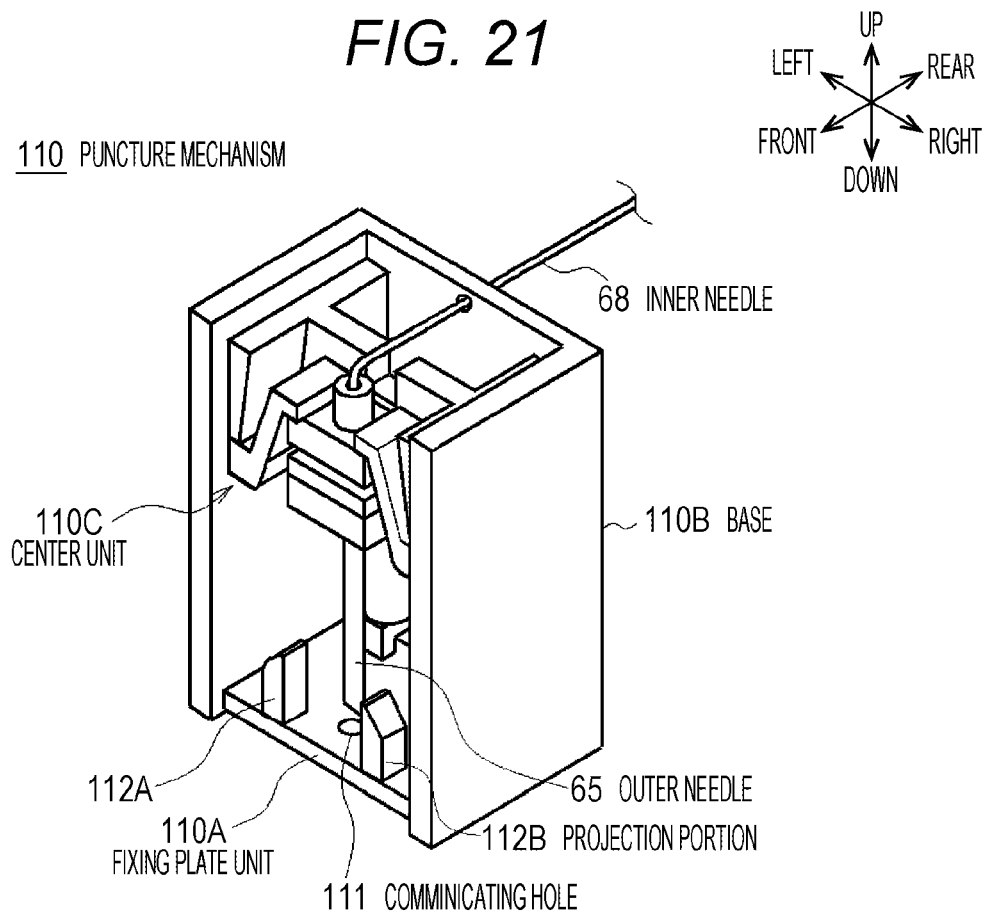
FIG. 21 is a diagram schematically illustrating the structure of a puncture mechanism according to a further different embodiment.

For example, a puncture mechanism 110 illustrated in FIG. 21 may be employed. The puncture mechanism 110 chiefly includes a fixing plate unit 110A, a base 110B projecting from the fixing plate unit 110A, and a center unit 110C capable of sliding in the up-down direction inside the base 110B. The puncture mechanism 110 includes the push-in unit 5A similar to the push-in unit 5A of the puncture mechanism 5, though the push-in unit 5A is not illustrated in FIG. 21.

The fixing plate unit 110A has a communicating hole 111 at the center of the fixing plate unit 110A. The communicating hole 111 communicates with the puncture needle hole 2B formed on the bottom surface 2A of the lower housing unit 2. Two projection portions 112A and 112B extending upward are provided on the left and right sides of the communicating hole 111, respectively, with a predetermined space left between the projection portions 112A and 112B.

The base 110B has a shape similar to the shape of the base 5C of the foregoing puncture mechanism 5 from which the concavities 59A and 59B are eliminated.

Figure 22:
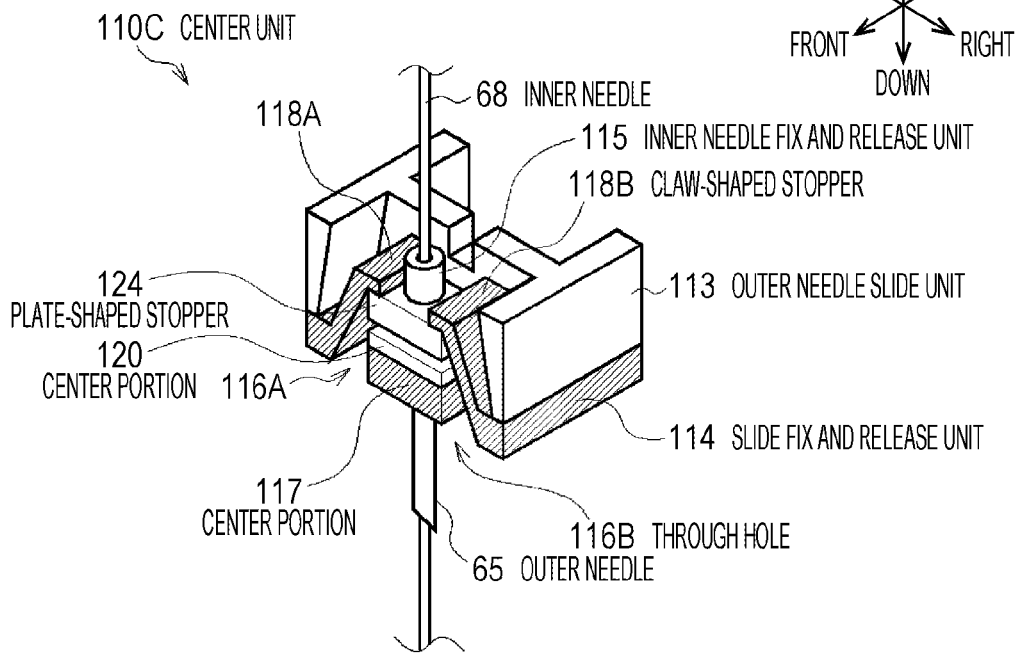
FIG. 22 is a diagram schematically illustrating the structure of a center unit according to the further different embodiment.

As illustrated in FIG. 22, the center unit 110C includes an outer needle slide unit 113 provided with the outer needle 65, a slide fix and release unit 114 (shaded portion in the figure) secured to the shaft 63 (not illustrated in the figure)

of the push-in unit 5A to fix or release the outer needle slide unit 113, and an inner needle fix and release unit 115 for fixing or releasing the inner needle 68 of the puncture needle.

The slide fix and release unit 114 is made of an elastic member. Through holes 116A and 116B are formed in the front part of the slide fix and release unit 114 with a predetermined space left between the through holes 116A and 116B through which the projection portions 112A and 112B of the fixing plate unit 110A are inserted in the left-right direction. A through hole (not shown) is further formed in a center portion 117 between the left and right through holes 116A and 116B. This through hole is a hole through which the outer needle of the outer needle slide unit 113 passes.

The slide fix and release unit 114 further includes a pair of claw-shaped stoppers 118A and 118B extending upward from the outer edges of the left and right through holes 116A and 116B to form a shape whose lower end is more opened to the outside than the upper end.

Figure 23A:
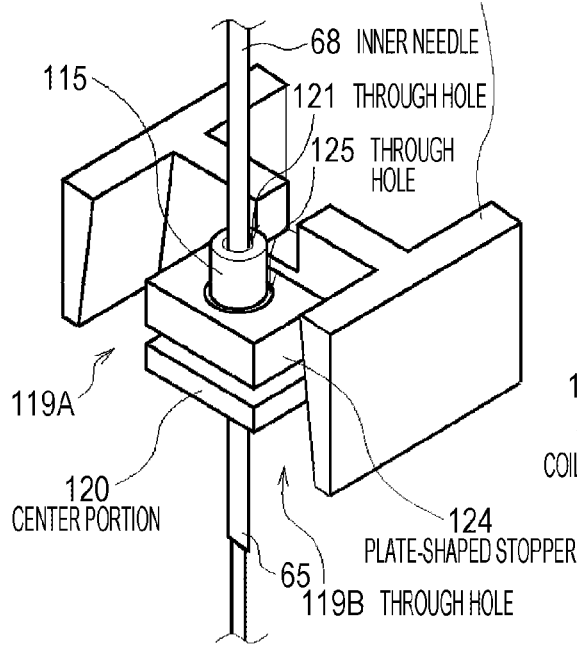
FIG. 23A is a front-side-top perspective view schematically illustrating conditions of fixation of an inner needle according to the further different embodiment.
Figure 23B:
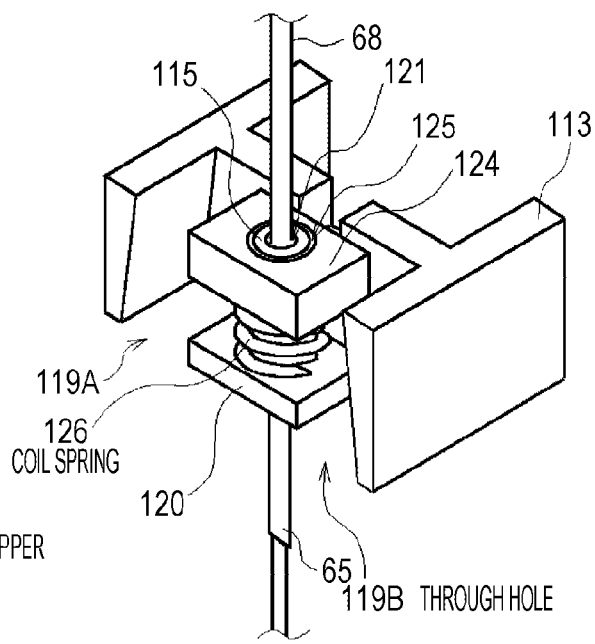
FIG. 23B is a front-side-top perspective view schematically illustrating release of fixation of an inner needle according to the further different embodiment.

As illustrated in FIGS. 23A and 23B as well as FIG. 22, through holes 119A and 119B are formed at the front end of the outer needle slide unit 113 with a predetermined space left between the through holes 119A and 119B through which the left and right claw-shaped stoppers 118A and 118B are inserted in the left-right direction of the slide fix and release unit 114. Furthermore, a through hole (not shown) is provided in a center portion 120 between the left and right through holes 119A and 119B. This through hole is a hole through which the inner needle 68 passes.

The metal outer needle 65 is further provided on the bottom surface of the center portion 120 of the outer needle slide unit 113. The outer needle 65 communicates with the through hole and projects downward.

Though not shown in the figure, the other end of the coil spring 85 of the outer needle slide unit 113 is fixed in a manner similar to the coil spring 85 of the outer needle slide unit 66 of the foregoing puncture mechanism 5.

Figure 23C:
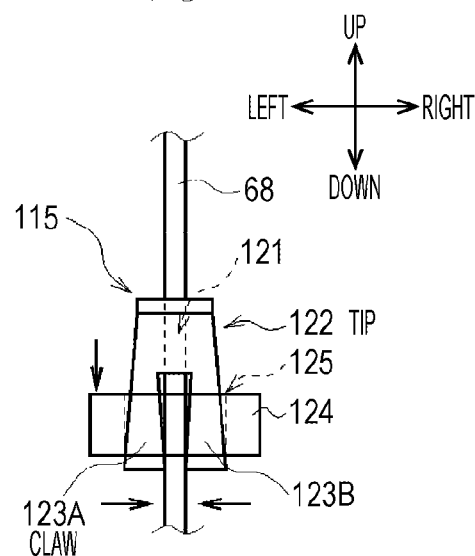
FIG. 23C is a perspective view schematically illustrating conditions of fixation of an inner needle according to the further different embodiment.
Figure 23D:
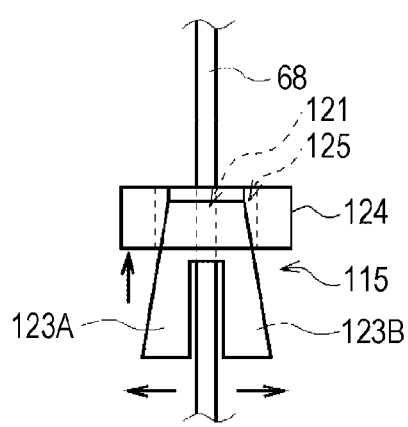
FIG. 23D is a perspective view schematically illustrating release of fixation of an inner needle according to the further different embodiment.

The inner needle fix and release unit 115 is made of an elastic member, and includes a cylindrical tip 122, and claws 123A and 123B as illustrated in FIGS. 23C-23D. The cylindrical tip 122 has a through hole 121 located at the center of the tip 122. The through hole 121 is a hole through which the inner needle passes. The claws 123A and 123B extend downward from the lower left end and right end of the tip 122 with a predetermined space left between the claws 123A and 123B. The left and right claws 123A and 123B form a shape whose lower end is more opened to the outside than the upper end.

The inner needle fix and release unit 115 is disposed on the center portion 120 of the outer needle slide unit 113. The inner needle 68 passes through the through hole 121 of the inner needle fix and release unit 115, further passes between the left and right claws 123A and 123B, and is inserted from the through hole (not shown) of the outer needle slide unit 113 into the outer needle 65.

Furthermore, a plate-shaped stopper 124 having a shape substantially similar to the shape of the center portion 120 of the outer needle slide unit 113 is further fitted to the inner needle fix and release unit 115.

The plate-shaped stopper 124 has a through hole 125 at the center of the plate-shaped stopper 124. The through hole 125 has substantially the same diameter as the outside diameter of the tip 122 of the inner needle fix and release unit 115. The plate-shaped stopper 124 is fitted to the inner needle fix and release unit 115 by insertion of the inner needle fix and release unit 115 into the through hole 125.

Furthermore, a coil spring 126 is fitted between the plate-shaped stopper 124 and the center portion 120 of the outer needle slide unit 113 in such a manner as to surround the outer circumference of the inner needle fix and release unit 115. This urges the plate-shaped stopper 124 upward toward the tip 122 side of the inner needle fix and release unit 115.

Suppose that the outer needle slide unit 113 is disposed on the slide fix and release unit 114 with the inner needle 68 inserted into the outer needle 65 of the outer needle slide unit 113 via the inner needle fix and release unit 115.

In this case, the center portion 120 of the outer needle slide unit 113 and the plate-shaped stopper 124 are sandwiched between the center portion 117 and the tip portions of the left and right claw-shaped stoppers 118A and 118B of the slide fix and release unit 114 as illustrated in FIG. 22. As a result, the outer needle slide unit 113 and the plate-shaped stopper 124 are fixed to the slide fix and release unit 114.

In this state, the plate-shaped stopper 124 is pushed toward the lower part of the inner needle fix and release unit 115. Consequently, the left and right claws 123A and 123B of the inner needle fix and release unit 115 are pressed toward the inside by the plate-shaped stopper 124 and deformed in such a manner as to decrease the space between the left and right claws 123A and 123B as illustrated in FIG. 23C.

As a result, the inner needle 68 is pressed from the left and right sides via the left and right claws 123A and 123B and fixed to the inner needle fix and release unit 115. Accordingly, the inner needle 68 is fixed to the outer needle slide unit 113.

Figure 24C:
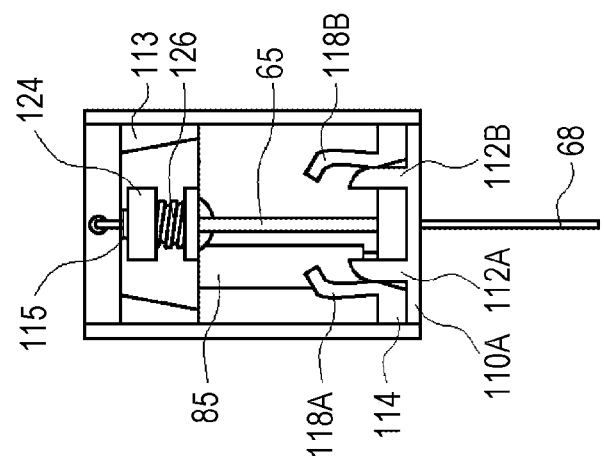
FIG. 24C is a diagram schematically describing operation of the puncture mechanism according to the further different embodiment in a third position.
Figure 24B:
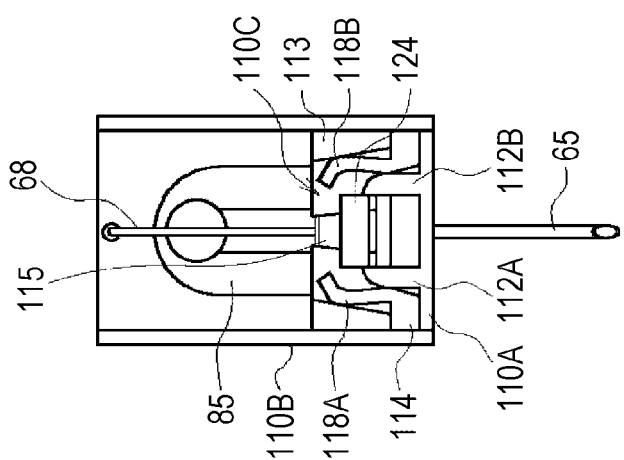
FIG. 24B is a diagram schematically describing operation of the puncture mechanism according to the further different embodiment in a second position.
Figure 24A:
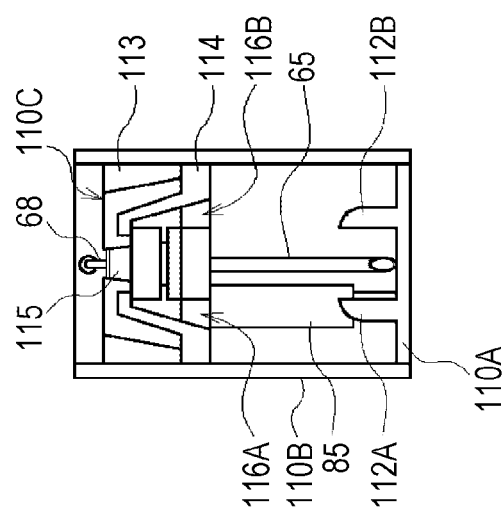
FIG. 24A is a diagram schematically describing operation of the puncture mechanism according to the further different embodiment in a first position.

As illustrated in FIG. 24A, the center unit 110C is positioned in the upper part of the base 110B while fixing the outer needle slide unit 113 to the slide fix and release unit 114, and fixing the inner needle 68 to the outer needle slide unit 113.

When the push-in unit 5A (not shown) is pushed in by the user under this condition, the center unit 110C begins sliding downward inside the base 110B.

In this case, the outer needle 65 of the center unit 110C slides downward while holding the inner needle 68 inside, and passes through the communicating hole 111 of the fixing plate unit 110A. Then, the outer needle 65 projects from the puncture needle hole 2B to be inserted into the body of the user together with the inner needle 68.

When the push-in unit 5A is completely pushed in and comes into such a condition that the center unit 110C reaches the lower end of the base 110B as illustrated in FIG. 24B, the left and right projection portions 112A and 112B of the fixing plate unit 110A are inserted into the left and right through holes 116A and 116B of the slide fix and release unit 114.

Moreover, the left and right projection portions 112A and 112B of the fixing plate unit 110A contact the inner surfaces of the left and right claw-shaped stoppers 118A and 118B of the slide fix and release unit 114, and push up the claw-shaped stoppers 118A and 118B. As a result, the left and right claw-shaped stoppers 118A and 118B open toward the outside. This condition releases the fixation between the slide fix and release unit 114 and the outer needle slide unit 113.

In this state, the downward pressing is released from the plate-shaped stopper 124 in accordance with the outward opening of the left and right claw-shaped stoppers 118A and 118B. Accordingly, the plate-shaped stopper 124 shifts toward the tip side of the inner needle fix and release unit 115 by the urging of the coil spring 126 as illustrated in FIG. 23B.

In this case, the inner needle fix and release unit 115 deforms in such a manner that the left and right claws 123A and 123B return to the original shapes, wherefore the space between the left and right claws 123A and 123B increases. This condition releases the fixation of the inner needle 68 sandwiched between the left and right claws 123A and 123B and fixed therebetween.

Accordingly, the puncture mechanism 110 releases the fixation between the slide fix and release unit 114 and the outer needle slide unit 113, and the fixation between the outer needle slide unit 113 and the inner needle 68 when the push-in unit 5A is completely pushed in.

More specifically, the left and right projection portions 112A and 112B of the fixing plate unit 110A functions as a release unit which releases the fixation between the slide fix and release unit 114 and the outer needle slide unit 113, and the fixation between the outer needle slide unit 113 and the inner needle 68 by contact between the projection portions 112A and 112B and the left and right claw-shaped stoppers 118A and 118B of the slide fix and release unit 114.

Then, as illustrated in FIG. 24C, the outer needle slide unit 113 slides upward together with the inner needle fix and release unit 115, and returns to the original position by the restoring force of the coil spring 85.

Accordingly, the entire outer needle 65 is removed from the inside of the body of the user, and accommodated within the chemical liquid supplying device 1 with the inner needle 68 indwelled within the body of the user.

Figure 25:
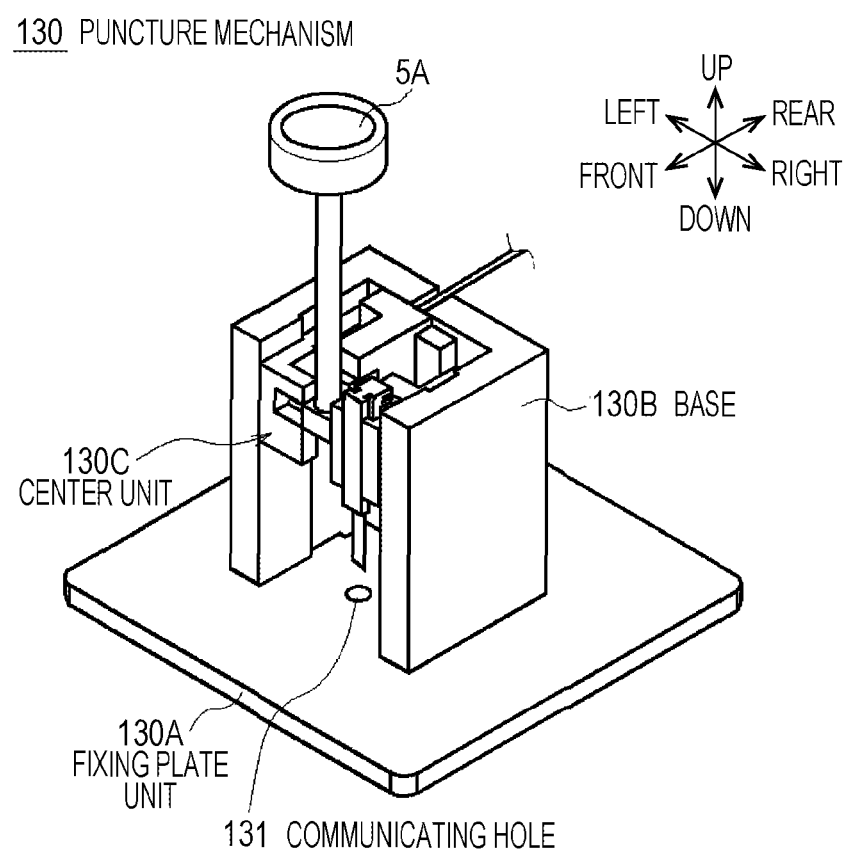
FIG. 25 is a diagram schematically illustrating the structure of a puncture mechanism according to a still further different embodiment.

Alternatively, a puncture mechanism 130 illustrated in FIG. 25 may be employed, for example, instead of the foregoing puncture mechanism 110. The puncture mechanism 130 chiefly includes a fixing plate unit 130A, a base 130B projecting from the fixing plate unit 130A, a center portion 130C capable of sliding in the up-down direction inside the base 130B, and the push-in unit 5A.

A communicating hole 131 communicating with the puncture needle hole 2B formed on the bottom surface 2A of the lower housing unit 2 is formed at the center of the fixing plate unit 130A.

The base 130B has a shape similar to the shape of the base 5C of the foregoing puncture mechanism 5 from which the concavities 59A and 59B are removed.

Figure 26C:
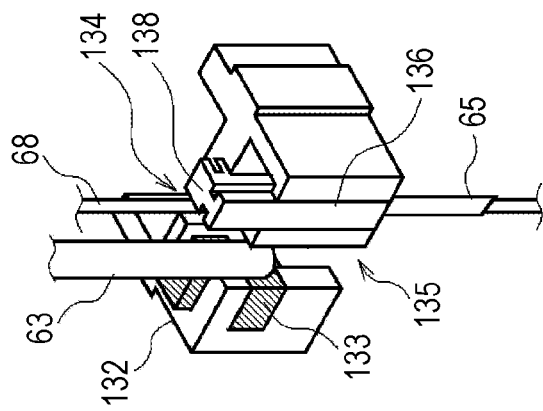
FIG. 26C is a diagram schematically illustrating the structure of a center unit according to the still further different embodiment in a third position.
Figure 26B:
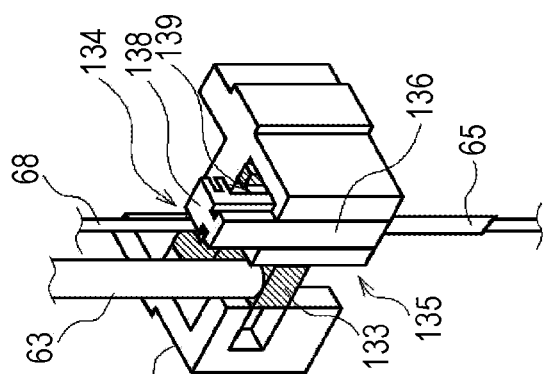
FIG. 26B is a diagram schematically illustrating the structure of a center unit according to the still further different embodiment in a second position.
Figure 26A:
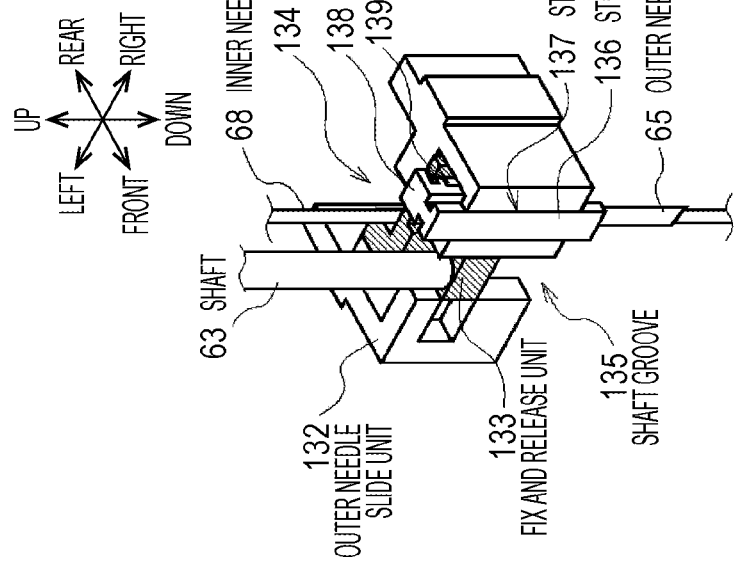
FIG. 26A is a diagram schematically illustrating the structure of a center unit according to the still further different embodiment in a first position.

As illustrated in FIGS. 26A-26C, a center unit 130C includes an outer needle slide unit 132 provided with the outer needle 65, and a fix and release unit 133 (shaded portion in the figure) which supports the shaft 63 of the push-in unit 5A, and fixes or releases the outer needle slide unit 132, and also fixes or releases the inner needle 68.

The outer needle slide unit 132 has a rectangular parallelepiped shape having a predetermined thickness. The outer needle 65 projects downward from the center of the bottom surface of the outer needle slide unit 132.

Though not illustrated in the figures, the outer needle slide unit 132 is attached to the coil spring 85 in a manner similar to the outer needle slide unit 66 of the foregoing puncture mechanism 5.

A notch 134 having a space wider than the outside diameter of the inner needle 68 is formed at the center of the upper surface of the outer needle slide unit 132. A through hole (not shown) communicating with the outer needle 65 is formed in the bottom of the notch 134. This through hole is a hole through which the inner needle 68 passes. The inner needle 68 is configured to pass through the notch 134, and enter the inside of the outer needle 65.

A groove (referred to as shaft groove) 135 is formed at the center of the front surface of the outer needle slide unit 132. The groove 135 extends from the upper end of the outer needle slide unit 132 to the lower end thereof. The groove 135 is a groove through which the shaft 63 of the push-in unit 5A passes.

A groove (referred to as stopper groove) 137 is further formed on the front surface of the outer needle slide unit 132. The groove 137 extends from the upper end of the outer needle slide unit 132 outside of the shaft groove 135 (such as right side) to the lower end of the outer needle slide unit 132 outside of the shaft groove 135. The groove 137 is a groove to which a stopper 136 is fitted.

The bar-shaped stopper 136 longer than the stopper groove 137 is fitted to the stopper groove 137 in such a condition as to freely slide in the up-down direction. A claw 138 projecting toward the rear is provided at the upper end of the stopper 136.

A fix and release unit 133 having an L-shaped cross section is further fitted to the inside of the outer needle slide unit 132 in such a condition as to freely slide in the left-right direction.

The fix and release unit 133 is configured to slide with the upper end of the fix and release unit 133 exposed from the upper surface of the outer needle slide unit 132. A concavity 139 fitted to the claw 138 of the stopper 136 is provided at the upper end of the fix and release unit 133.

As illustrated in FIGS. 26A-26B, the fix and release unit 133 is so configured that the front end of the fix and release unit 133 enters the inside of the shaft groove 135 of the outer needle slide unit 132 and closes the shaft groove 135 when the fix and release unit 133 is positioned on the side close to the stopper 136 (right side). In this state, a part of the fix and release unit 133 comes close to the side surface of the notch 134 of the outer needle slide unit 132 such that the inner needle 68 positioned between the fix and release unit 133 and the notch 134 can be sandwiched and fixed between the fix and release unit 133 and the side surface of the notch 134.

On the other hand, when the fix and release unit 133 is positioned on the opposite side (left side) as illustrated in FIG. 26C, the front end of the fix and release unit 133 separates from the shaft groove 135 and does not close the shaft groove 135. Simultaneously, the front end of the fix and release unit 133 separates from the side surface of the notch 134 and does not fix the inner needle 68.

Moreover, the fix and release unit 133 is urged toward the side (left side) away from the stopper groove 137 by a compression spring (not shown) provided within the outer needle slide unit 132.

The stopper 136 is configured to fix the fix and release unit 133 to the right side and hold the fix and release unit 133 on the right side. More specifically, the stopper 136 fixes the fix and release unit 133 to the right side and holds the fix and release unit 133 on the right side by fitting the claw 138 to the concavity 139 of the fix and release unit 133 from above with the fix and release unit 133 pressed toward the right side.

When the fix and release unit 133 is fixed and held in this manner, the lower end of the stopper 136 projects downward from the bottom surface of the outer needle slide unit 132.

The center unit 130C fixes the fix and release unit 133 to the right inside the outer needle slide unit 132 and holds the fix and release unit 133 on the right inside the outer needle slide unit 132 in this manner. Simultaneously, the center unit 130C is disposed in the upper part of the base 130B with the inner needle 68 fixed to the outer needle slide unit 132 as illustrated in FIG. 27A.

In this state, the lower end of the shaft 63 of the push-in unit 5A contacts the upper surface of the front end of the fix and release unit 133 closing the shaft groove 135 of the outer needle slide unit 132.

When the push-in unit 5A is pushed in by the user in this condition, the upper surface of the front end of the fix and release unit 133 is pressed downward by the shaft 63 of the push-in unit 5A. As a result, the entire center unit 130C is pressed downward and starts sliding downward inside the base 130B.

In this state, the outer needle 65 of the center unit 130C slides downward while holding the inner needle 68 inside. Then, the outer needle 65 passes through the communicating hole 131 of the fixing plate unit 130A, and projects from the puncture needle hole 2B to be inserted into the body of the user together with the inner needle 68.

When the push-in unit 5A is completed pushed in as illustrated in FIG. 27B, the center unit 130C reaches the lower end of the base 130B.

In this state, the lower end of the stopper 136 projecting downward from the bottom surface of the outer needle slide unit 132 contacts the fixing plate unit 130A before the bottom surface of the outer needle slide unit 132 contacts the fixing plate unit 130A. Accordingly, after the contact of the lower end of the stopper 136, the outer needle slide unit 132 slides relative to the stopping stopper 136.

Then, as illustrated in FIG. 26B, the claw 138 of the stopper 136 fitted to the concavity 139 of the fix and release unit 133 separates in the upward direction from the concavity 139, whereby the fixation of the fix and release unit 133 to the right side is released.

As a result, the fix and release unit 133 slides toward the left inside the outer needle slide unit 132 by the effect of the compression spring as illustrated in FIG. 26C.

Then, the front end of the fix and release unit 133 separates from the shaft groove 135 and disconnects from the shaft 63. Consequently, the downward pressing applied to the center unit 130C is released. In this state, a part of the fix and release unit 133 separates from the side surface of the notch 134 of the outer needle slide unit 132, whereby the fixation of the inner needle 68 sandwiched between the fix and release unit 133 and the notch 134 is released.

Accordingly, when the push-in unit 5A of the puncture mechanism 130 is completely pushed in, the fixation between the center unit 130C and the shaft 63 of the push-in unit 5A is released. Simultaneously, the fixation between the center unit 130C and the inner needle 68 is released.

More specifically, according to the puncture mechanism 130, the fixing plate unit 130A functions as a release unit for releasing the fixation between the center unit 130C and the shaft 63, and the fixation between the center unit 130C and the inner needle 68 by contact between the fixing plate unit 130A and the stopper 136 of the center unit 130C.

Then, the center unit 130C slides upward and returns to the original position by the restoring force of the coil spring 85 while sliding the shaft 63 of the push-in unit 5A along the shaft groove 135 as illustrated in FIG. 27C.

As a result, the entire outer needle 65 is removed from the inside of the body of the user and accommodated within the chemical liquid supplying device 1 with the inner needle 68 indwelled within the body of the user.

According to the description herein, the two types of the puncture mechanisms 110 and 130 have been discussed. However, other mechanisms may be employed as long as these puncture mechanisms can insert the puncture needle and retract the outer needle by the push-in operation of the push-in unit 5A.

Other Embodiment 3

According to the foregoing embodiment, the coil spring 85 is used as an elastic member for retracting only the outer needle 65 into the chemical liquid supplying device 1 after insertion of the puncture needle containing the metal outer needle 65 and the resin inner needle 68 into the body of the user. However, elastic members other than the coil spring 85 may be employed as long as these elastic members function in similar manners as the coil spring 85.

What is claimed is:

1. A puncture device comprising:
   a puncture needle including an outer needle and an inner tube located in the outer needle;
   a housing unit accommodating the puncture needle; and
   a puncture mechanism located within the housing unit, the puncture mechanism including:
      a push-in unit configured to be pushed in with respect to the housing unit,
      an outer needle slide unit attached to the outer needle and configured to slide within the housing unit, the outer needle slide unit comprising first and second arms that are bendable between a first position at which the inner tube is gripped by the first and second arms and a second position at which the inner tube is released by the first and second arms,
      a stopper providing releasable fixation between the push-in unit and the outer needle slide unit and releasable fixation between the inner tube inserted into the outer needle and the outer needle slide unit,
      an elastic member, a first end of which is fixed to the housing unit and a second end of which is fixed to the outer needle slide unit, and
      a fixation release unit configured to release the fixation between the push-in unit and the outer needle slide unit and the fixation between the outer needle slide unit and the inner tube,
   wherein, when the push-in unit is pushed in under the condition of fixation between the push-in unit and the outer needle slide unit, and fixation between the outer needle slide unit and the inner tube, the outer needle containing the inner tube therein projects from the housing unit in accordance with sliding of the outer needle slide unit in a first direction, and
   wherein, when the outer needle slide unit slides to a predetermined position, the outer needle is retracted into the housing unit while the inner tube remains projected from the housing, in accordance with release of the fixation between the push-in unit and the outer needle slide unit and the fixation between the outer needle slide unit and the inner tube, and in accordance with sliding of the outer needle slide unit in a second direction by operation of the elastic member.

2. The puncture device according to claim 1, wherein the fixation release unit contacts the stopper to release the fixation between the push-in unit and the outer needle slide unit, and the fixation between the outer needle slide unit and the inner needle.

3. The puncture device according to claim 1, wherein the push-in unit is configured such that, when the push-in unit is pushed in, the push-in unit acts as a cover of the housing unit to close the housing unit and provide a water-proof structure.

4. The puncture device according to claim 1, further comprising:
   a sensor attached to a tip of the inner tube of the puncture needle, and a controller configured to obtain information from the sensor.

5. The puncture device according to claim 4, further comprising a transmission unit configured to transmit the information obtained from the sensor.

6. The puncture device according to claim 1, wherein the elastic member is a spring.

7. The puncture device according to claim 1, wherein the stopper comprises a plurality of levers each having a U-shaped cross section.

8. The puncture device according to claim 1, wherein the outer needle is made of a metal material, and the inner tube is made of a resin material.

9. A chemical liquid supplying device comprising:
a puncture needle including an outer needle and an inner tube located in the outer needle;
a housing unit accommodating the puncture needle;
a puncture mechanism located within the housing unit;
a chemical liquid storage unit configured to store a chemical liquid; and
a delivery unit configured to deliver the chemical liquid from the chemical liquid storage unit via the inner tube,
wherein the puncture mechanism includes:
a push-in unit configured to be pushed in with respect to the housing unit,
an outer needle slide unit attached to the outer needle and configured to slide within the housing unit, the outer needle slide unit comprising first and second arms that are bendable between a first position at which the inner tube is gripped by the first and second arms and a second position at which the inner tube is released by the first and second arms,
a stopper providing releasable fixation between the push-in unit and the outer needle slide unit and releasable fixation between the inner tube inserted into the outer needle and the outer needle slide unit,
an elastic member, a first end of which is fixed to the housing unit and a second end of which is fixed to the outer needle slide unit, and
a fixation release unit configured to release the fixation between the push-in unit and the outer needle slide unit, and the fixation between the outer needle slide unit and the inner tube,
wherein, when the push-in unit is pushed in under the condition of fixation between the push-in unit and the outer needle slide unit, and fixation between the outer needle slide unit and the inner tube, the outer needle containing the inner tube therein projects from the housing unit in accordance with sliding of the outer needle slide unit in a first direction, and
wherein, when the outer needle slide unit slides to a predetermined position, the outer needle is retracted into the housing unit while the inner tube remains projected from the housing, in accordance with release of the fixation between the push-in unit and the outer needle slide unit and the fixation between the outer needle slide unit and the inner tube, and in accordance with sliding of the outer needle slide unit in a second direction by operation of the elastic member.

10. The chemical liquid supplying device according to claim 9, wherein the housing comprises an attachment portion for attaching the device to the skin of a user.

11. The chemical liquid supplying device according to claim 10, wherein the chemical liquid storage unit comprises a cylinder and a piston.

12. The chemical liquid supplying device according to claim 11, wherein the chemical liquid storage unit comprises a regulation portion that has a diameter smaller than the main body of the cylinder.

13. The chemical liquid supplying device according to claim 9, wherein the delivery unit comprises a piston, a cylinder unit, a cover unit, a unidirectional valve, an X ring, an X ring fixing unit, and a fixing member.

14. The chemical liquid supplying device according to claim 13, further comprising a drive unit configured to drive the piston of the delivery unit.

15. The chemical liquid supplying device according to claim 14, wherein the drive unit comprises a motor and a bearing unit.

16. The chemical liquid supplying device according to claim 15 wherein the motor comprises a motor shaft with screw grooves that interface with a screw hole in the bearing unit such that the bearing unit is linearly moveable when the motor shaft rotates.

17. The chemical liquid supplying device according to claim 9, further comprising a central processing unit, a read only memory, a random access memory, a power source unit, an interface unit, and a notification unit.

18. The chemical liquid supplying device according to claim 17, wherein the interface unit comprises a button.

19. The chemical liquid supplying device according to claim 17, further comprising a drive unit, wherein the central processing unit is configured to control the drive unit in accordance with set parameters.

20. The chemical liquid supplying device according to claim 9, wherein the outer needle is made of a metal material, and the inner tube is made of a resin material.

* * * * *